(12) United States Patent
Lisanti et al.

(10) Patent No.: US 12,188,936 B2
(45) Date of Patent: Jan. 7, 2025

(54) BIOMARKERS AND THERAPEUTICS FOR ENDOCRINE THERAPY RESISTANCE

(71) Applicant: LUNELLA BIOTECH, INC., Ottawa (CA)

(72) Inventors: Michael P. Lisanti, Manchester (GB); Federica Sotgia, Manchester (GB); Marco Fiorillo, Manchester (GB)

(73) Assignee: LUNELLA BIOTECH, INC., Ontario (CA)

( * ) Notice: Subject to any disclaimer, the term of this patent is extended or adjusted under 35 U.S.C. 154(b) by 287 days.

(21) Appl. No.: 15/734,030

(22) PCT Filed: May 30, 2019

(86) PCT No.: PCT/US2019/034575
§ 371 (c)(1),
(2) Date: Dec. 1, 2020

(87) PCT Pub. No.: WO2019/232161
PCT Pub. Date: Dec. 5, 2019

(65) Prior Publication Data
US 2021/0215702 A1  Jul. 15, 2021

Related U.S. Application Data

(60) Provisional application No. 62/679,379, filed on Jun. 1, 2018.

(51) Int. Cl.
| | |
|---|---|
| *G01N 33/574* | (2006.01) |
| *A61K 31/138* | (2006.01) |
| *A61K 31/404* | (2006.01) |
| *A61K 31/454* | (2006.01) |
| *A61K 31/4725* | (2006.01) |
| *A61K 31/496* | (2006.01) |
| *A61K 31/498* | (2006.01) |
| *A61K 31/519* | (2006.01) |
| *A61K 31/538* | (2006.01) |
| *A61K 31/65* | (2006.01) |

(52) U.S. Cl.
CPC ..... *G01N 33/57488* (2013.01); *A61K 31/138* (2013.01); *A61K 31/404* (2013.01); *A61K 31/454* (2013.01); *A61K 31/4725* (2013.01); *A61K 31/496* (2013.01); *A61K 31/498* (2013.01); *A61K 31/519* (2013.01); *A61K 31/538* (2013.01); *A61K 31/65* (2013.01)

(58) Field of Classification Search
CPC ............................................. G01N 33/57488
See application file for complete search history.

(56) References Cited

U.S. PATENT DOCUMENTS

| | | |
|---|---|---|
| 2012/0039805 A1 | 2/2012 | Lisanti et al. |
| 2014/0026234 A1 | 1/2014 | Lisanti et al. |
| 2014/0322705 A1 | 10/2014 | Lisanti et al. |
| 2015/0252430 A1 | 9/2015 | Bryant et al. |

FOREIGN PATENT DOCUMENTS

| | | | | |
|---|---|---|---|---|
| WO | WO-2018195434 A1 * | 10/2018 | ........... | A61K 31/341 |
| WO | WO-2019108729 A1 * | 6/2019 | ........... | A61K 31/122 |

OTHER PUBLICATIONS

Zhang et al. Cell Cycle, 2017, vol. 16, No. 8, pp. 737-745 (Year: 2017).*
Harrod et al. (Oncogene, 2017, vol. 36, p. 2286-2296) (35 total pages w/ Supplemental Table) (Year: 2017).*
Li et al. Cell Reports, Sep. 26, 2013, vol. 4, p. 1116-1130 (Year: 2013).*
International Search Report for PCT/US2019/03575 dated Aug. 27, 2019, 4 pages.
Written Opinion of the ISA for PCT/US2019/03575 dated Aug. 27, 2019, 16 pages.
International Preliminary Report on Patentability for PCT/US2019/03575 dated Jun. 8, 2020, 21 pages.
Martinez-Outschoorn et al., "Anti-estrogen resistance in breast cancer is induced by the tumor microenvironment and can be overcome by inhibiting mitochondrial function in epithelial cancer cells", Cancer Biol Ther, Nov. 15, 2011, vol. 12, pp. 924-938.
Fanning et al., "Estrogen receptor alpha somatic mutations Y537S and D538G confer breast cancer endocrine resistance by stabilizing the activating function-2 binding conformation", eLife, Feb. 2, 2016, vol. 5, e12792, pp. 1-25.
Sotgia et al., "Mitochondria "fuel" breast cancer metabolism: fifteen markers of mitochondrial biogenesis label epithelial cancer cells, but are excluded from adjacent stromal cells," Cell Cycle, Nov. 21, 2012, vol. 11, pp. 4309-4401.
Sotgia et al., "Mitochondrial markers predict recurrence, metastasis and tamoxifen-resistance in breast cancer patients: Early detection of treatment failure with companion diagnostics," Oncotarget, Sep. 15, 2017, vol. 8, pp. 68730-68745.
Wang Junjian et al.: "Reprogramming metabolism by histone methyltransferase NSD2 drives endocrine resistance via coordinated activation of pentose phosphate pathway enzymes", Cancer Letters, New York, NY, US, vol. 378, No. 2, May 6, 2016 (May 6, 2016), pp. 69-79, XP029567768, ISSN: 0304-3835, DOI: 10.1016/J.CANLET.2016.05.004.

(Continued)

*Primary Examiner* — James D. Anderson
(74) *Attorney, Agent, or Firm* — Nixon & Vanderhye, P.C.

(57) ABSTRACT

Cancer cells can develop resistance to endocrine therapies, such as Tamoxifen, through acquisition of the Y537S mutation. Cells transfected with the Y537S mutation showed significant increases in mitochondrial mass and membrane potential, consistent with an increase in mitochondrial biogenesis. Certain biomarkers are identified that have prognostic value of endocrine therapy resistance. The mechanism resulting in this resistance, however, leaves these treatment-resistant cells vulnerable to therapeutics that inhibit mitochondrial biogenesis. Numerous mitochondrial biogenesis inhibitors are disclosed, as well as methods for reducing or eliminating endocrine treatment resistance, improving the effectiveness of an endocrine therapy, and for treating cancer.

35 Claims, 11 Drawing Sheets

(56) References Cited

OTHER PUBLICATIONS

Anonymous: "Affymetrix GeneChip Human Genome U133 Array Set HGU133A", NCBI, GEO, Platform GPL96, Mar. 11, 2002 (Mar. 11, 2002), pp. 1-511, XP055546924, Retrieved from the Internet: URL:https://www.ncbi.nlm.nih.gov/geo/query/acc.cgi?acc=GPL96 [retrieved on Jan. 24, 2019].

Bela Ozsvari et al.: "Mitoriboscins: Mitochondrial-based therapeutics targeting cancer stem cells (CSCs), bacteria and pathogenic yeast", Oncotarget, vol. 8, No. 40, Sep. 15, 2017 (Sep. 15, 2017), pp. 67457-67472, XP055546993, DOI: 10.18632/oncotarget.19084.

Musgrove Elizabeth A et al.: "Biological determinants of endocrine resistance in breast cancer", Nature Reviews Cancer, Nature Pub. Group, London, vol. 9, No. 9, Sep. 1, 2009 (Sep. 1, 2009), pp. 631-643, XP037553065, ISSN: 1474-175X, DOI: 10.1038/NRC2713 [retrieved on Sep. 1, 2009].

Fanning et al.: "Estrogen receptor alpha somatic mutations Y537S and D538G confer breast cancer endocrine resistance by stabilizing the activating function-2 binding conformation", eLife, vol. 5, Feb. 2, 2016 (Feb. 2, 2016), pp. 1-25, XP055659664.

Sotgia et al.: "A mitochondrial based oncology platform for targeting cancer stem cells (CSCs): MITO-ONC-RX", Cell Cycle, vol. 17, No. 17, Sep. 2, 2018, pp. 2091-2100, XP055750287.

\* cited by examiner

BIOMARKERS AND THERAPEUTICS FOR ENDOCRINE THERAPY RESISTANCE

This application is the U.S. national phase of International Application No. PCT/US2019/034575 filed May 30, 2019 which designated the U.S. and claims priority to U.S. Provisional Application No. 62/679,379 filed Jun. 1, 2018, the entire contents of each of which are hereby incorporated by reference.

STATEMENT REGARDING GOVERNMENT SUPPORT

None.

BACKGROUND

Field of the Invention

The present disclosure relates to biomarkers prognostic of cancer cell resistance to endocrine therapies such as Tamoxifen, and therapeutic agents to overcome such resistance.

Introduction

Endocrine therapy is broadly defined as a treatment that adds, blocks, or removes hormones. Hormones can cause certain cancers (such as prostate and breast cancer) to grow, and synthetic hormones or other drugs may be given to block the body's natural hormones and slow or halt the tumor progression. In human breast cancer patients, the hormone estrogen and its main receptor ESR1 are key drivers of tumor initiation, cancer progression and ultimately metastasis. As a consequence, targeted endocrine therapies, such as Tamoxifen, were first developed to inhibit estrogen receptor signaling in ER(+) breast cancer cells. Historically, Tamoxifen represents one of the earliest forms of targeted therapy and was first clinically trialed in the 1970's, at the Christie Hospital in Manchester, UK. Unfortunately, however, endocrine therapy ultimately fails in a significant number of patients on long-term anti-estrogen therapy, due to the acquired emergence of drug-resistance. The resulting treatment failure often has dire consequences for the patient, with the emergence of tumor recurrence and distant metastasis, resulting in poor clinical outcomes.

If we are going to successfully prevent or reverse treatment failure, we need to know the underlying mechanism(s) by which ER(+) tumor cells can successfully escape the effects of endocrine therapy. Until recently, the prominent role of somatic mutations in the estrogen receptor in conferring resistance to endocrine therapy has remained largely unappreciated. These somatic mutations can significantly change the conformation and functional activity of the estrogen receptor, effectively locking it in a constitutively-activated state. Two of the most common mutations, namely Y537S and D538G, both allow the estrogen receptor to bind coactivators, in the absence of the estrogen ligand, resulting in a constitutively-active receptor.

What is needed, then, is an improved understanding of the mechanism by which cancer cells develop resistance to endocrine therapy. Further, biomarkers having prognostic value of endocrine therapy resistance are needed. What is also needed are therapeutic agents effective at suppressing and/or eliminating endocrine therapy resistance in cancer cells.

BRIEF SUMMARY

This disclosure describes the mechanisms through which cells acquire resistance to endocrine therapies, such as Tamoxifen (e.g., Nolvadex, Soltamox), biomarkers prognostic of cancer cell resistance to endocrine therapies, and therapeutic agents that may be administered to reduce or eliminate endocrine therapy resistance. As such, the present approach may be used in conjunction with endocrine treatments, and as part of cancer therapy, and in particular breast cancer therapy. Although several embodiments below relate to Tamoxifen-resistant cell lines, the present approach may be applied to other endocrine therapies. For example, other common endocrine therapy drugs for breast cancer treatment include: Abemaciclib (Verzenio), Anastrozole (Arimidex), Exemestane (Aromasin), Fulvestrant (Faslodex), Goserelin (Zoladex), Letrozole (Femara), Leuprorelin, leuprolide acetate (Lupron), Megestrol (Megace), Palbociclib (Ibrance), and Toremifene (Fareston).

Naturally-occurring somatic mutations in the estrogen receptor gene (ESR1) have been previously implicated in the clinical development of resistance to endocrine therapies, such as Tamoxifen. For example, the somatic mutation Y537S has been specifically associated with acquired endocrine therapy resistance and a more aggressive clinical phenotype in breast cancer patients, resulting in tumor recurrence and distant metastasis.

This disclosure relates to the biomarkers having prognostic value of endocrine therapy resistance, and therapeutic agents effective for overcoming such resistance. As described in more detail below, a genetic cell model was used to better understand the molecular mechanism(s) underlying the drug-resistance behavior. Recombinantly-transduced MCF7 cells with a lentiviral vector encoding ESR1 (Y537S) were used as the genetic cell model. A panel of other isogenic MCF7 cell lines was generated in parallel, as negative controls. As a first step, MCF7-ESR1 (Y537S) cells were confirmed to be functionally resistant to Tamoxifen, as compared with vector alone controls. Importantly, further phenotypic characterization of these Y537S cells revealed an increased resistance to Tamoxifen-induced apoptosis, allowing them to form mammospheres with higher efficiency, in the presence of Tamoxifen. Metabolic flux analysis of the Y537S cells revealed a hyper-metabolic phenotypic, with significantly increased mitochondrial respiration (>3-fold) and high ATP production (~2-fold), as well as enhanced aerobic glycolysis (~1.75-fold). In further support of the hyper-metabolic state, the Y537S cells showed significant increases in mitochondrial mass and membrane potential, consistent with an increase in mitochondrial biogenesis.

Y537S cells were subjected to unbiased label-free proteomics analysis to identify which molecular signaling pathways may be hyper-activated. Results indicated that a Rho-GDI/PTEN signaling pathway was selectively activated by the Y537S mutation. Remarkably, this profile is nearly identical in MCF7-TAMR cells; these cells were independently-generated in vitro, by using increasing step-wise concentrations of Tamoxifen. The striking similarities between the proteomic profiles and phenotypes of Y537S cells and TAMR cells suggests a highly conserved mechanism underlying Tamoxifen-resistance.

The Y537S mutation is specifically associated with the over-expression of a number of protein markers of poor clinical outcome. In summary, this disclosure presents a novel metabolic mechanism leading to endocrine therapy resistance, which has important clinical implications for improving patient outcomes through novel, targeted therapies.

The present approach may take the form of a method for identifying and treating endocrine therapy resistance in a cancer. A biological sample of the cancer may be obtained, and the level of at least one biomarker prognostic of endocrine therapy resistance in the biological sample may be determined. Alternatively, the biomarker level(s) may be determined by an outside laboratory or third party, and provided for analysis. The determined level may be compared to a threshold level for the at least one biomarker. The threshold level may be obtained from published literature or other sources for a normal cell, as are available and/or known in the art. A pharmaceutically effective amount of at least one mitochondrial biogenesis inhibitor may be administered if the determined level exceeds the threshold level. In some embodiments, the threshold level(s) may be determined from in vivo data for patients having cancer but not having endocrine treatment failure (e.g., patients without tumor recurrence or distant metastasis).

The biomarker prognostic of endocrine therapy resistance may be at least one of (i) a biomarker prognostic of tumor recurrence, and/or (ii) a biomarker prognostic of distant metastasis. In some embodiments, the biomarker prognostic of endocrine therapy resistance is at least one of HSPD1, GRPEL1, MRPL15, MRPS16, COX4I1, ENO1 and ENO2. In addition to having prognostic value of resistance to endocrine therapy, these biomarkers also have prognostic value for distant metastasis and tumor recurrence, particularly with respect to breast cancers and cells having the Y537S mutation. In some embodiments, the biomarker may be at least one of HSPD1, MRPL15, MRPL4, AKAP1, PTRH2, COX4I1, GRPEL1, HSPA9, MRPS16, ENO1, TALD01, TIGAR, ENO1, and ENO2.

In the present approach, the mitochondrial biogenesis inhibitor may be or include at least one of a mitoriboscin, the combination of an oxidative metabolism inhibitor and a glycolytic metabolism inhibitor, a repurposcin, an antimitoscin, a mitoketoscin, a mitoflavoscin, a mitoflavin, a TPP-derivative, and an MDIVI-1 derivative. For example, the mitochondrial biogenesis inhibitor may be a mitoriboscin having one of the following general structures:

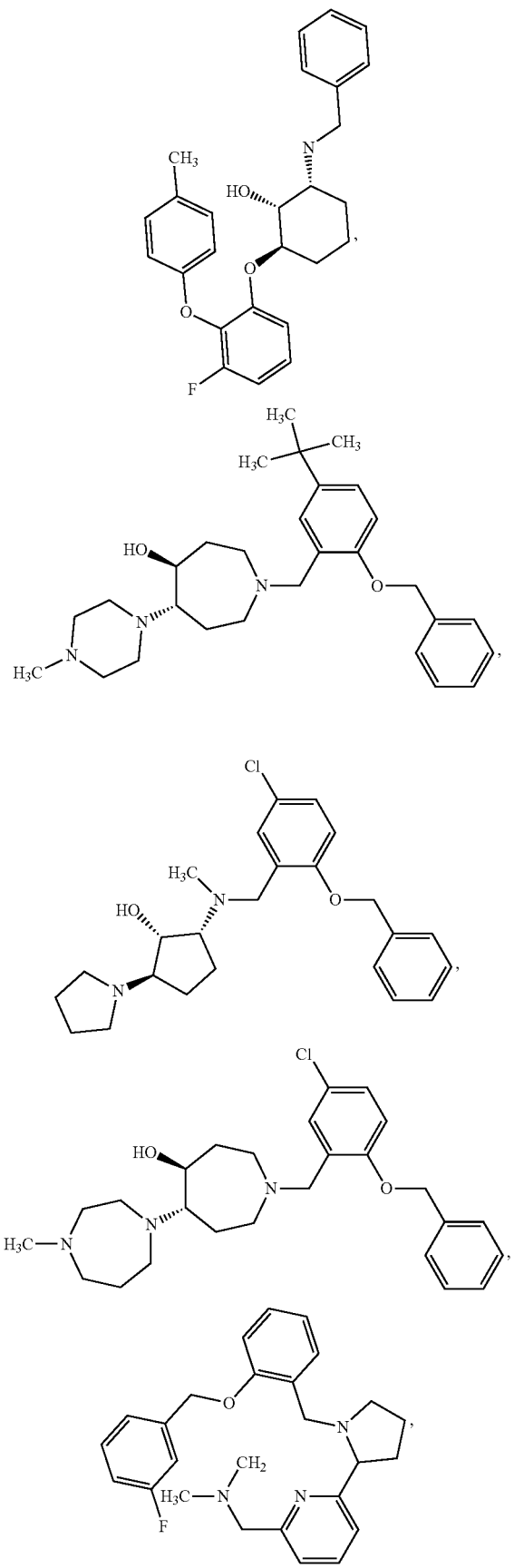

-continued

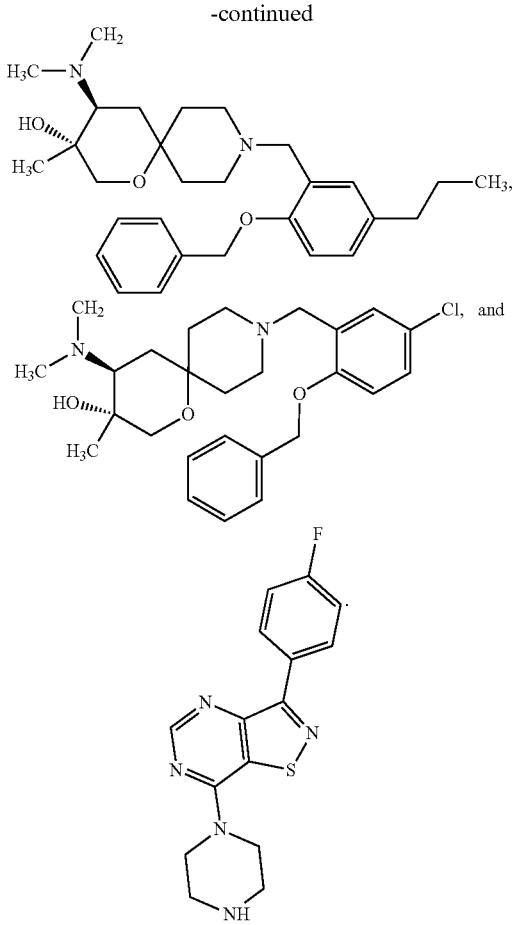

In some embodiments of the present approach, the mitochondrial biogenesis inhibitor may be or include a combination of (i) an oxidative metabolism inhibitor selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and (ii) a glycolytic metabolism inhibitor selected from the group comprising: a glycolysis inhibitor, an OXPHOS inhibitor, and an autophagy inhibitor. In some embodiments, the glycolytic metabolism inhibitor is at least one of (i) a glycolysis inhibitor comprising one of 2-deoxy-glucose, ascorbic acid, and stiripentol; (ii) an OXPHOS inhibitor comprising one of atoravaquone, irinotecan, sorafenib, niclosamide, and berberine chloride; and (iii) an autophagy inhibitor comprising chloroquine. In a demonstrative embodiment, the mitochondrial biogenesis inhibitor is a combination of doxycycline, azithromycin, and ascorbic acid.

Some embodiments of the present approach may use one or more antimitoscins as a mitochondrial biogenesis inhibitor. The antimitoscin may be a member of the tetracycline family, a member of the erthyromycin family, chloramphenicol, pyrvinium pamoate, atovaquone, and bedaquiline, wherein the antibiotic has been chemically modified with at least one mitochondrial targeting signal. Examples of mitochondrial targeting signals include palmitic acid, stearic acid, myristic acid, oleic acid, a short-chain fatty acid, a medium-chain fatty acid, a lipophilic cation, tri-phenyl-phosphonium, a derivative of tri-phenyl-phosphonium, guanidinium, a guanidinium derivative, and 10-N-nonyl acridine orange. A TPP-derivative may be selected from the group comprising 2-butene-1,4-bis-TPP; derivatives of 2-butene-1,4-bis-TPP; 2-chlorobenzyl-TPP; derivatives of 2-chlorobenzyl-TPP; 3-methylbenzyl-TPP; derivatives of 3-methylbenzyl-TPP; 2,4-dichlorobenzyl-TPP; derivatives of 2,4-dichlorobenzyl-TPP; 1-naphthylmethyl-TPP; derivatives of 1-naphthylmethyl-TPP; p-xylylenebis-TPP; and derivatives of p-xylylenebis-TPP. It should be appreciated that under the present approach, one or more of the mitochondrial biogenesis inhibitors may be chemically modified with a mitochondrial targeting signal, such as described above.

One or more mitoketoscins may be used as the mitochondrial biogenesis inhibitor in some embodiments, alone or in combination with other agents. The mitoketoscin may have one of the following general formula:

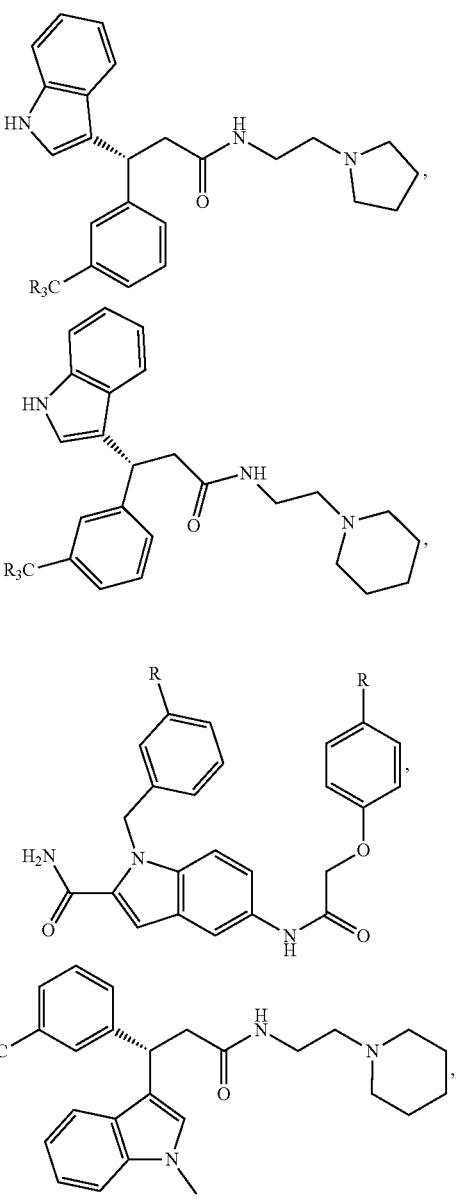

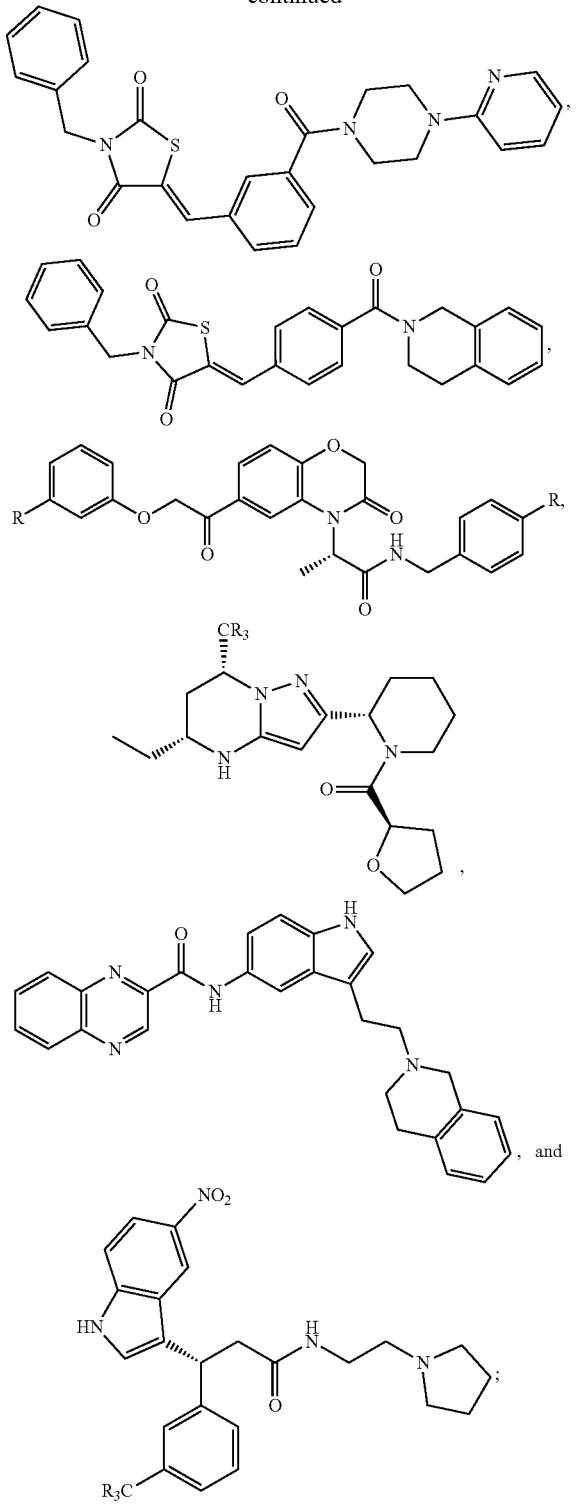

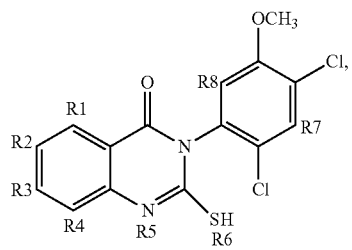

or a pharmaceutically acceptable salt thereof, wherein each R may be the same or different, and may be selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, and benzoic acid-based derivatives.

In some embodiments, the mitochondrial biogenesis inhibitor may be or include a mitoflavoscin and/or a mitoflavin. Diphenyleneiodonium chloride is an example of a mitoflavoscin, and roseoflavin, lumichrome, alloxazine, lumiflavine, 1,5-dihydroriboflavin, and 1,5-dihydroflavin are examples of mitoflavins.

The mitochondrial biogenesis inhibitor in some embodiments may be or include an MDIVI-1 derivative having the general formula:

or a pharmaceutically acceptable salt thereof, wherein each of R1 through R8 may be selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, benzoic acid-based derivatives, and a mitochondrial targeting signal such as those discussed above.

In some embodiments, the mitochondrial biogenesis inhibitor may be or include a repurposcin. Examples of reporuposcins include, but are not limited to, berberine chloride, quercetin, niclosamide, acriflavinium hydrochloride, sorafenib, emetine dihydrochloride, dactinomycin, plicamycin, suloctidil, teniposide, pentamidine isethionate, daunorubicin, thioguanine, amsacrine, phenformin hydrochloride, irinotecan hydrochloride, mitomycin, hydroxyprogesterone caproate, cyclosporine, lanatoside c, mercaptopurine, quinacrine hydrochloride, fenofibrate, neomycin, puromycin, rapamycin, everolimus, G418, trovafloxacin, levofloxacin, avocatin B, clarithromycin, ciprofloxacin, spiramycin, telithromycin, norfloxacin, moxifloxacin, ofloxacin, minocycline, tetracycline, demethylchlortetracycline, a member of the tetracycline family, a member the erthyromycin family, clindamycin, metronidazole, linezolid, mupirocin, vancomycin, clindamycin, cephalosporin, ciprofolxacin, streptomycin, amoxicillin, and azelaic acid, wherein the compound is chemically modified with at least one mitochondrial targeting signal.

The present approach may also take the form of increasing the effectiveness of an endocrine therapy. Generally, a biological sample of the cancer may be obtained and have the level of at least one biomarker prognostic of endocrine therapy resistance in the biological sample determined. The biomarker level may be compared to a threshold level for the at least one biomarker. A pharmaceutically effective amount of at least one mitochondrial biogenesis inhibitor may be administered if the determined level exceeds the threshold level. The mitochondrial biogenesis inhibitor may be administered in conjunction with the endocrine therapeutic (e.g., Tamoxifen), such as simultaneously, or prior to the endocrine therapeutic. For example, the mitochondrial biogenesis inhibitor may be administered 1-4 hours before the endocrine therapeutic, or in some embodiments the mitochondrial biogenesis inhibitor may be administered on a daily basis for several days before the endocrine therapeutic.

It should also be appreciated that the present approach may take the form of a method for treating cancer. Generally, a biological sample of the cancer may be obtained and have the level of at least one biomarker prognostic of endocrine therapy resistance in the biological sample determined. The biomarker level may be compared to a threshold level for the at least one biomarker. A pharmaceutically effective amount of at least one mitochondrial biogenesis inhibitor may be administered if the determined level exceeds the threshold level. The mitochondrial biogenesis inhibitor may be administered in conjunction with other cancer therapies, such as other chemotherapeutic agents, radiation therapy, and other therapies known in the art.

The present approach may also take the form of treating breast cancer, and in particular breast cancer having a resistance to endocrine therapies, through the administration of at least one mitochondrial biogenesis inhibitor. In some embodiments, the mitochondrial biogenesis inhibitor may be administered to a patient having an up-regulated expression of one or more biomarkers or gene products as described herein. In some embodiments, the mitochondrial biogenesis inhibitor may be administered in conjunction with an endocrine therapy, and may be used to increase the endocrine therapy's effectiveness. It should be appreciated that the present approach may take other forms, consistent with the disclosure.

DESCRIPTION OF THE DRAWINGS

FIG. 5A shows OCR data, and FIGS. 5B-5D show basal respiration, maximal respiration, and ATP production, respectively.

FIG. 5A shows ECAR data, and FIGS. 6B-6D show glycolysis, glycolytic capacity, and glycolytic reserve capacity, respectively.

DETAILED DESCRIPTION

Figure 1:
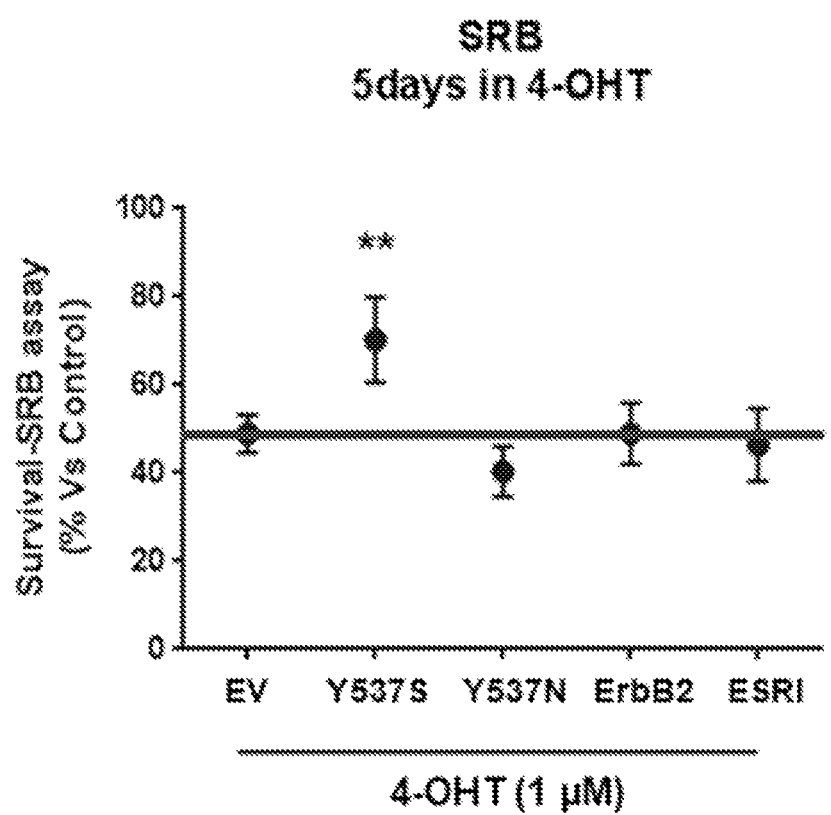
FIG. 1 shows the results of an SRB Survival assay for various MCF7-transduced cells over a 5-day exposure to 1 µM 4-OHT.

The following description includes various embodiments of the present approach, relating to the mechanisms through which cells acquire Tamoxifen resistance, biomarkers prognostic of Tamoxifen resistance and related tumor recurrence and/or distant metastasis, and therapeutics for reducing and eliminating Tamoxifen resistance. It should be appreciated that the present approach applies to endocrine therapies, and therefore references to Tamoxifen resistance are not intended to be limiting unless otherwise stated. Other examples of endocrine therapy drugs for breast cancer treatment include: Abemaciclib (Verzenio), Anastrozole (Arimidex), Exemestane (Aromasin), Fulvestrant (Faslodex), Goserelin (Zoladex), Letrozole (Femara), Leuprorelin, leuprolide acetate (Lupron), Megestrol (Megace), Palbociclib (Ibrance), and Toremifene (Fareston)

The data and analysis disclosed herein addresses how the Y537S mutation promotes resistance to Tamoxifen. For brevity, this disclosure refers to Tamoxifen resistance, but it should be appreciated that the disclosure applies to other endocrine therapies. Somatic mutations in the estrogen receptor gene are specifically associated with the onset and development of endocrine therapy resistance in human breast cancer patients. In particular, the Y537S mutation drives endocrine therapy resistance by maintaining the estrogen receptor in the constitutively activated state, resulting in an aggressive and hyper-metabolic clinical phenotype, leading to tumor recurrence and distant metastasis. As a result, mitochondrial biogenesis is a target for overcoming Tamoxifen resistance.

The new cellular model of endocrine therapy resistance described herein models the gain-of-function effects afforded by the acquisition of the Y537S mutation. The cDNA encoding the mutated ESR1 (Y537S) gene was inserted into MCF7 human breast cancer cells using a lentiviral vector. As negative controls, a series of other isogenic MCF7 cell lines, harboring the wild-type estrogen receptor and the empty-vector (EV), were also generated. The expression of the ESR1 (Y537S) mutant was functionally validated as sufficient to experimentally confer Tamoxifen-resistance, relative to other control cell lines, tested side-by-side. The Y537S mutant conferred drug-resistance to Tamoxifen-induced cell apoptosis, allowing the efficient formation of 3D tumor spheroids, even in the presence of Tamoxifen.

The Y537S mutation confers an abnormal metabolic phenotype, reflecting a form of gene-induced metabolic re-programming. In particular, by using the Seahorse XFe96 metabolic flux analyzer, the effects of the Y537S mutation were determined on the i) oxygen consumption rate (OCR) and ii) the extracellular acidification rate (ECAR), as well as ATP production. The Y537S mutation resulted in a hyper-metabolic state, accompanied by elevated rates of mitochondrial respiration, enhanced ATP levels and increased glycolysis. Consistent with these findings, the Y537S mutation also increased mitochondrial mass and membrane potential, reflecting an increase in mitochondrial biogenesis. Inhibiting mitochondrial biogenesis reverses the effect of the mutation, and increases the effectiveness of Tamoxifen therapy.

Unbiased proteomics analysis was carried out to identify the key metabolic targets that were increased by the Y537S mutation. Ultimately, over 30 nuclear-encoded mitochondrial proteins were found to be over-expressed, as well as greater than 9 enzymes linked to glycolysis and the pentose-phosphate pathway. The Y537S mutation was also linked to the over-expression of a number of protein biomarkers of poor clinical outcome (TIGAR, COL6A3, ERBB2, STAT5, AFP, TFF1, CDK4, CD44). Ingenuity Pathway Analysis independently demonstrated that the proteomic profile of MCF7-Y537S cells is very similar to MCF7-TAMR cells, another Tamoxifen-resistant cell line created by chronic exposure to Tamoxifen. Both cell lines show the hyper-activation of a Rho-GDI/PTEN signaling pathway. These novel mechanism(s) driving Tamoxifen-resistance clearly have important implications for significantly improving clinical outcomes for breast cancer patients.

This disclosure provides a description of the phenotypic effects of the Y537S mutation on MCF7 cells in culture. For this purpose, a genetic model in MCF7 cells was created by stably over-expressing the ESR1 cDNA carrying the Y537S mutation. Importantly, the results show that the Y537S mutation confers a hyper-active phenotype, due to the metabolic re-programming of mitochondrial function and the glycolytic pathway, resulting in increased ATP production and resistance to apoptosis, effectively protecting cancer stem cells (CSCs) from the anti-mitochondrial effects of Tamoxifen. Interestingly, Tamoxifen also functions as an inhibitor of mitochondrial complex I activity. Therefore, it is perhaps not surprising that Tamoxifen resistance could be achieved, by the ability of the Y537S mutation to effectively augment mitochondrial "power." High levels of key mitochondrial markers, including complex I proteins, are specifically-associated with Tamoxifen-resistance in human breast cancer patients.

The inventors generated a genetic model of Tamoxifen-resistance using MCF7-Y537S cells. Somatic mutations of the human estrogen receptor alpha (ESR1) have been directly implicated in the pathogenesis of endocrine therapy resistance in human breast cancer patients. However, the exact mechanism(s) by which these ESR1 mutations induce Tamoxifen-resistance remains largely unknown. To begin to dissect how these mutations phenotypically confer drug resistance, the inventors constructed an in vitro genetic model, using MCF7 cells, an ER(+) breast cancer cell line.

Briefly, MCF7 cells were transduced with a lentiviral vector carrying the Y537S mutation of ESR1 and positive "pools" of cells were selected, using a puromycin resistance cassette. Four other isogenic MCF7 cells lines were also generated in parallel, which served as negative controls for these experiments: ESR1 (WT and Y537N), ErbB2, and empty-vector (EV).

Lentiviral transduction with the ESR1 (Y537S) mutation is sufficient to stably confer Tamoxifen-resistance in MCF7 cell monolayers. To directly determine the validity of our model system, MCF7-Y537S cells were cultured for 5 days in the presence of Tamoxifen (1 μM) to assess its effect on cell viability. FIG. 1 shows the results of an SRB Survival assay for various MCF7-transduced cells over a 5-day exposure to 1 μM 4-OHT. MCF7 cells were stably-transduced with either ESR1 (WT, Y537S, or Y537N) or ErbB2 (HER2), to genetically create a clinically relevant model of endocrine therapy resistance. Vector alone control MCF7 cells were generated in parallel (empty vector; EV; p-EV-105-puroR), as a negative control. Note that MCF7-Y537S cells clearly show resistance to 4-OHT at 1 μM, as FIG. 1 indicates a significantly higher survival percentage relative to the control. The SRB assay was performed as a measure of cell viability and the experiment was carried out for 5 days. In contrast, 4-OHT has significant inhibitory effects on the viability of the other MCF7 cell lines. For FIG. 1, ** indicates p<0.005.

It should be appreciated that FIG. 1 shows that only MCF7-Y537S cells manifest a Tamoxifen-resistance phenotype, while all the other MCF7 cell lines tested retained Tamoxifen sensitivity. These findings provide the necessary evidence for the use of MCF7-Y537S cells as a valid genetic model of Tamoxifen-resistance. Since the Y537N mutation did not drive Tamoxifen resistance in this context, other micro-environmental factors may be needed to observe this phenotype.

The results show that Y537S drives resistance to Tamoxifen-induced apoptosis, enhancing mammosphere formation. An additional mechanism by which the Y537S mutation may contribute to Tamoxifen-resistance is its potential effect(s) on "stemness" and/or apoptosis. To test this hypothesis, first the potential effects on CSC propagation were assessed, using the mammosphere assay. In the absence of Tamoxifen, the Y537S mutation had no effect on mammosphere formation. However, in the presence of Tamoxifen, the Y537S mutation significantly promoted mammosphere formation, by nearly 2-fold. However, similar effects were also observed with the wild-type ESR1. Quantitation of these results is presented in FIGS. 2A-2C, and FIG. 3 includes representative images.

Figure 2A:
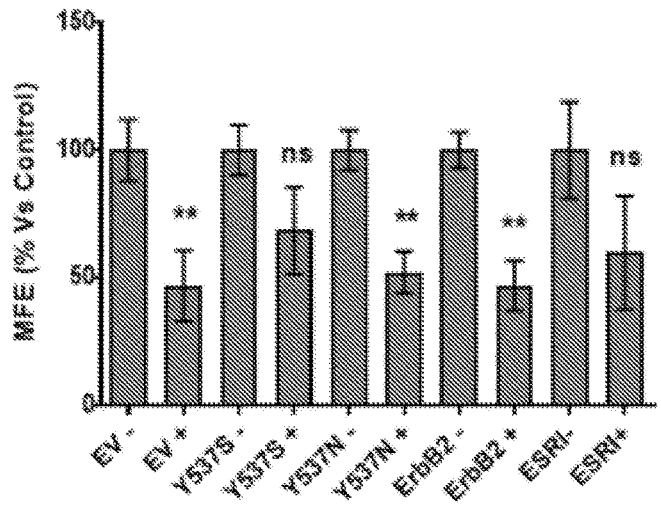
FIGS. 2A-2C show mammosphere formation assay results.
Figure 2B:
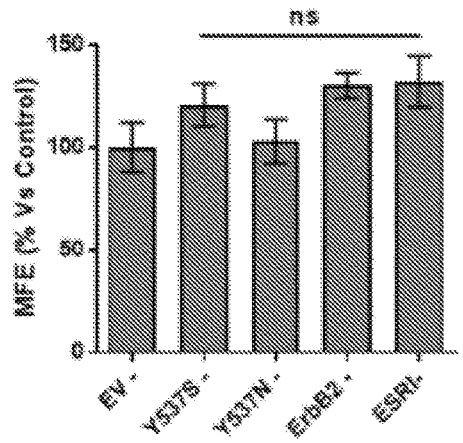
Figure 2C:
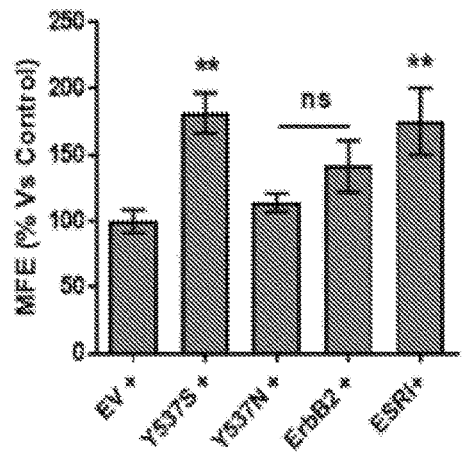

FIGS. 2A-2C show data for mammosphere formation assays and demonstrate that MCF7-Y537S cells are resistant to the inhibitory effects of Tamoxifen on mammosphere formation. FIG. 2A compares cells treated with 4-OHT (+) with untreated cells (−); FIG. 2B compares transfected cells with (("EV")); Panel C: Treated with 4-OHT. Mammosphere formation assays that generated these data were carried out for 5 days, in 6 well-plates, under low-attachment conditions. All of the transfected MCF7 cell lines were grown as mammospheres. A 72-hour pre-treatment with 4-OHT (1 μM) inhibited mammosphere formation efficiency (MFE) in all transfected cell lines, with the exception of MCF7-Y537S and MCF7-ESR1 (WT) cells. In contrast, no changes in mammosphere formation were observed in the absence of 4-OHT (1 μM) pre-treatment. In these figures, ** indicates p<0.005; and ns indicates not significant as evaluated by Student's t test.

Figure 3:
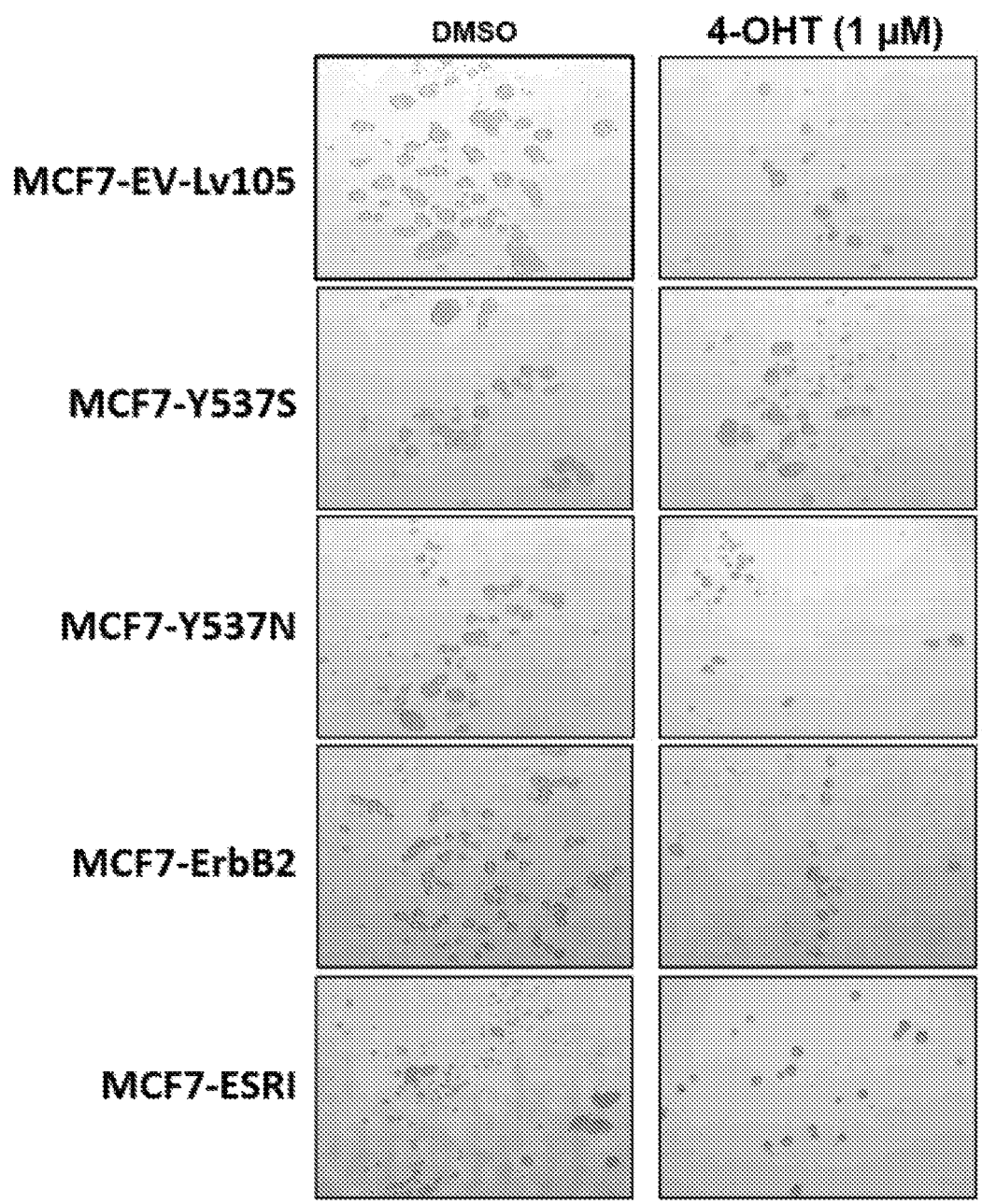
FIG. 3 is a comparison of MCF7-transduced cells in DMSO (left) versus the same cells in 1 µM 4-OHT (right).

FIG. 3 shows a comparison of MCF7-transduced cells after 72-hour pre-treatment in either vehicle alone (DMSO) or 1 μM 4-OHT. The images were captured with an Olympus microscope (4× objective, bright field), and demonstrate that the MCF7-Y537S cells are resistant to the inhibitory effects of Tamoxifen during mammosphere formation. Note that overall 4-OHT (1 μM) treatment reduced mammosphere formation; however, MCF7-Y537S cells remain largely unaffected as can be seen from the comparative images.

Figure 4A:
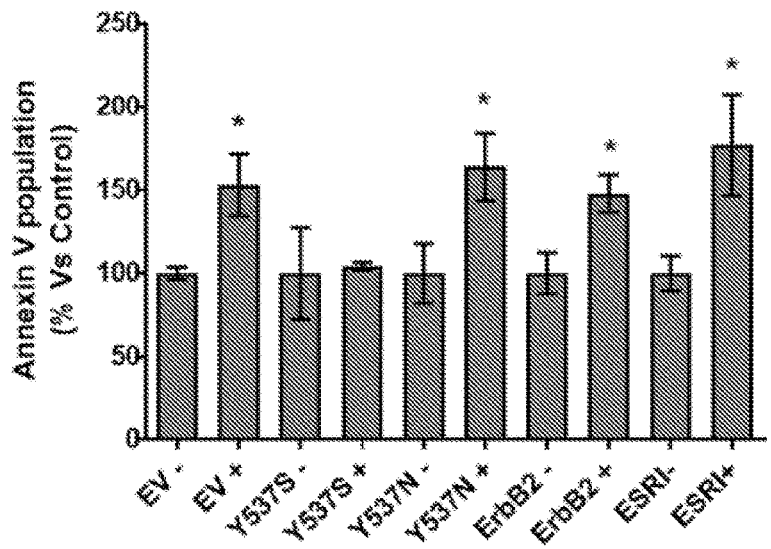
FIGS. 4A-4C show annexin V population level data in transfected cell lines.
Figure 4B:
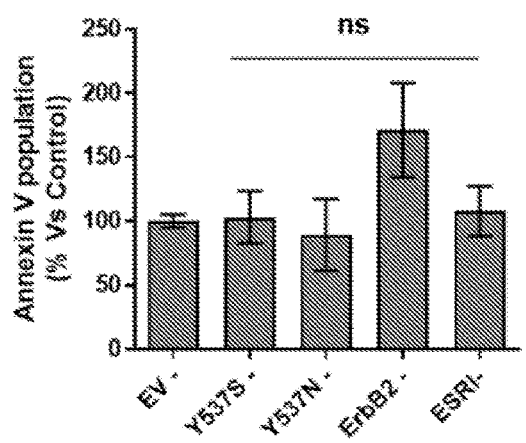
Figure 4C:
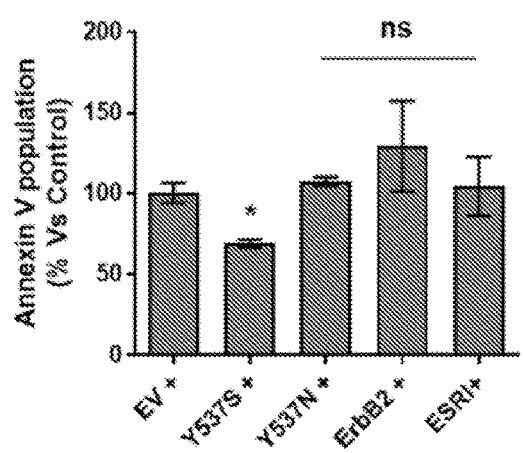

One mechanism by which the Y537S mutation may promote mammosphere formation in the presence of Tamoxifen is by conferring resistance to apoptosis. Staining with annexin V may be used to detect apoptotic cells by its ability to bind to phosphatidylserine, a marker of apoptosis when it is on the outer leaflet of the plasma membrane. Increases in annexin V staining indicates an increase in apoptosis. FIGS. 4A-4C highlight that the Y537S mutation significantly reduces annexin-V staining in the presence of Tamoxifen, as revealed by FACS analysis, consistent with apoptosis resistance. FIG. 4A shows annexin-V populations for the MCF-7 transduced cells, wherein the + indicates 72-hour pretreatment in 4-OHT (1 μM) for the MCF7-transduced cells. FIG.

4B shows transfected but untreated cells compared to the EV control, and FIG. 4C compares the pretreated cells to the pretreated EV control.

The data in FIGS. 4A-4C were obtained as follows. The transduced MCF7 cell lines were all plated in 6-well plates. On the next day, the cells were treated with 4-OHT (1 µM) for 72 hours. MCF7-EV cells were processed in parallel, as a negative control. Bar-graphs in FIGS. 4A-4C show the overall results, and FIG. 4A shows that MCF7-Y537S cells are resistant to the pro-apoptotic effects of 4-OHT. Note that annexin V levels were increased in all transfected cell lines. However, MCF7-Y537S cells were specifically resistant to the pro-apoptotic effects of 4-OHT. For the data in these drawings, * indicates $p<0.05$. In contrast, no changes in Annexin V levels were observed in all transfected cells, in the absence of 4-OHT (1 µM); ns=not significant.

The Y537S mutation confers a hyper-metabolic phenotype, with increased mitochondrial function and ATP production, elevated mitochondrial biogenesis and enhanced glycolysis. Further analysis demonstrated that one phenotypic mechanism by which the Y537S mutation may confer Tamoxifen-resistance is via the process of metabolic re-programming. The Y537S cells were subjected to metabolic phenotyping with the Seahorse XFe96 metabolic flux analyzer. FIGS. 5A-5D and 6A-6D show the results of these studies.

Figure 5A:
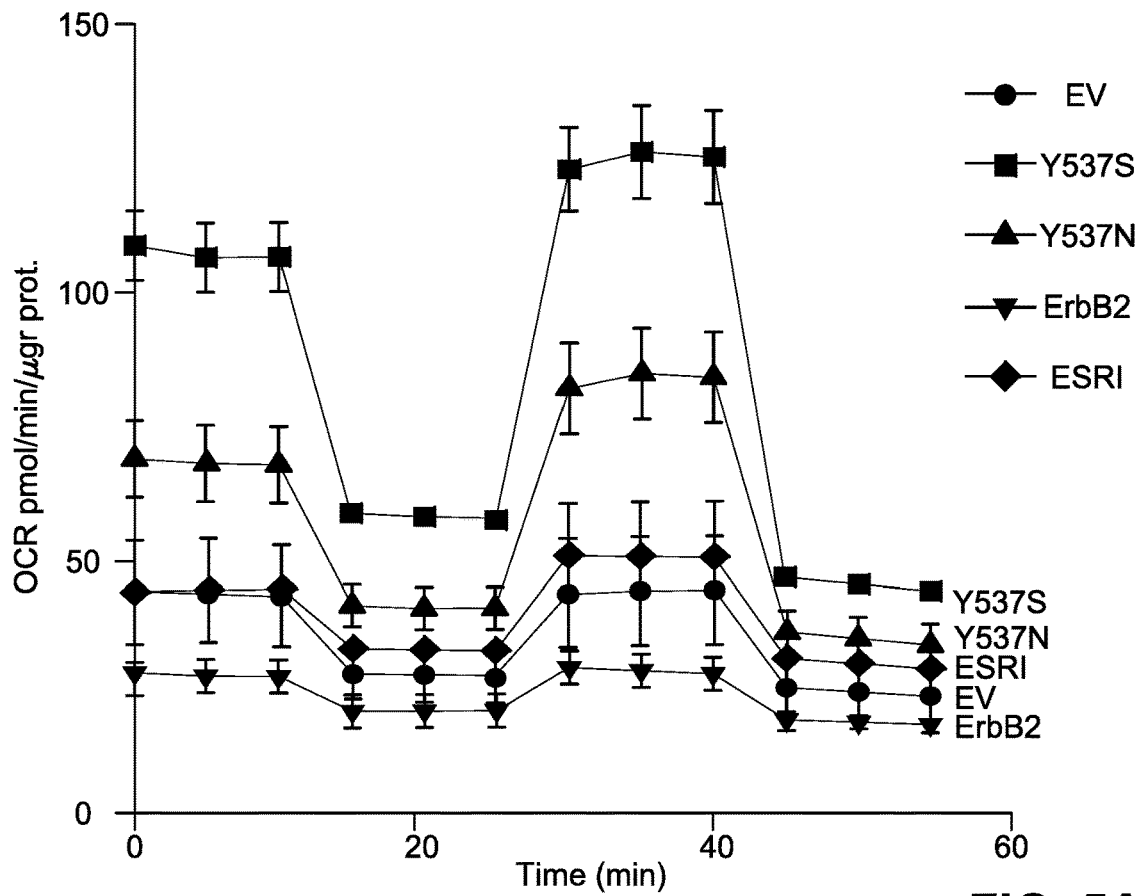
FIGS. 5A-5D show oxygen consumption rate (OCR) and ATP production data in the transfected cell lines. Specifically.
Figure 5B:
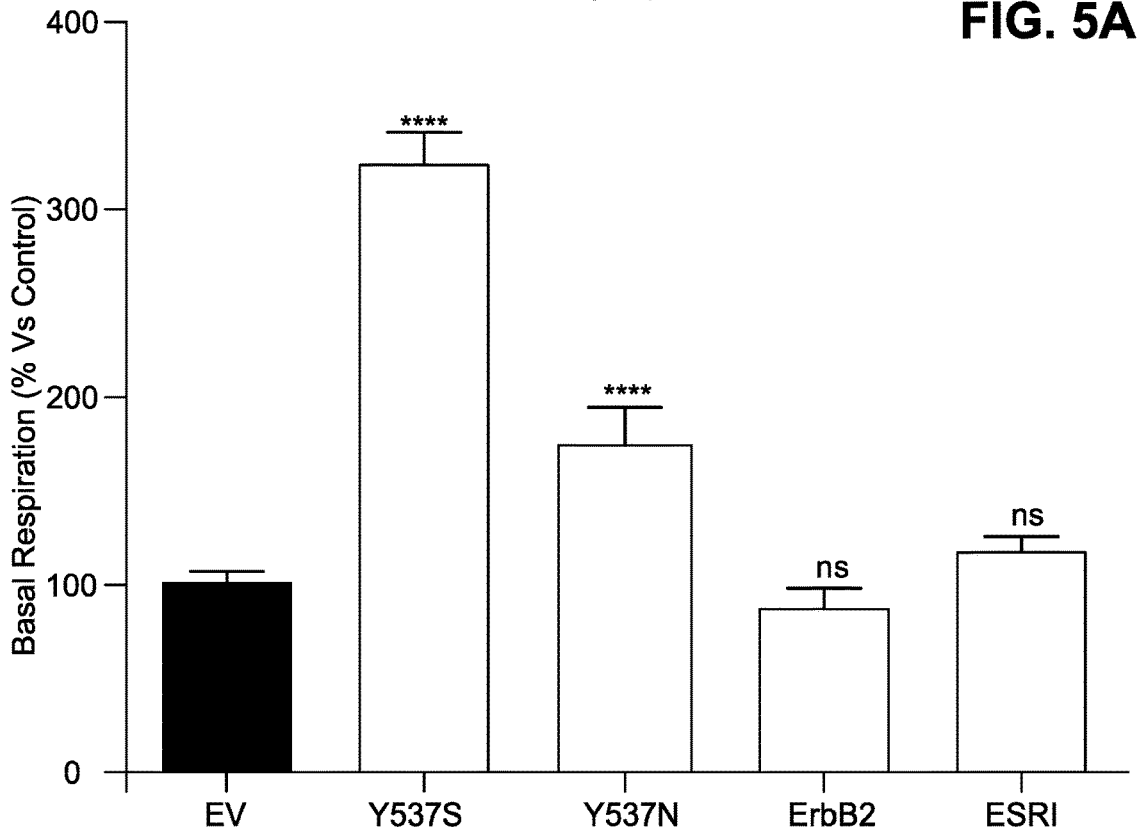
Figure 5C:
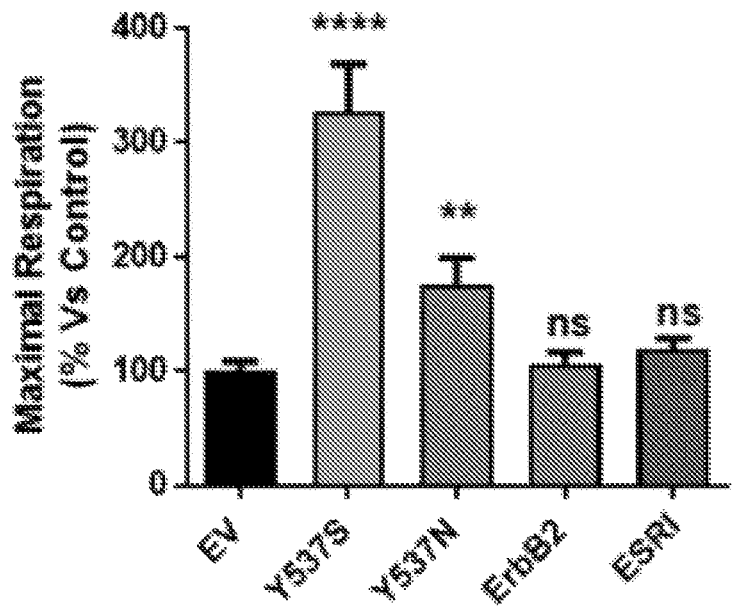
Figure 5D:
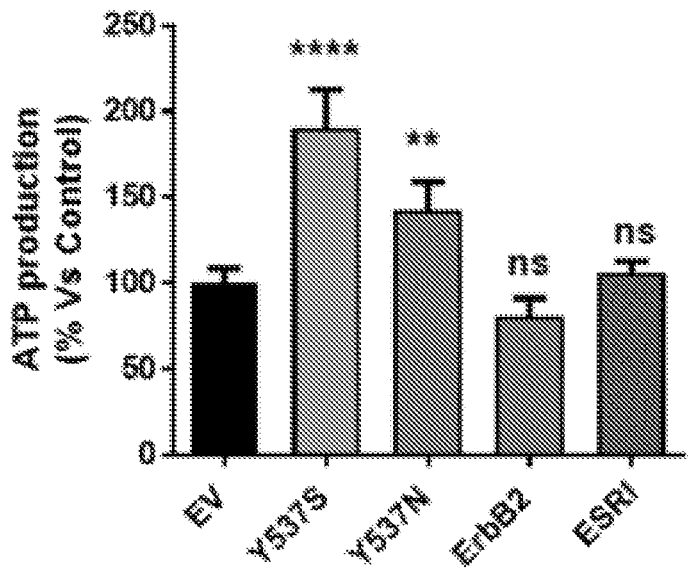

FIGS. 5A-5D show oxygen consumption rate (OCR) and ATP production data in the transfected cell lines. These data show a significant increase in mitochondrial OCR and ATP production in MCF7-Y537S cells. A Seahorse XFe96 metabolic-flux analyzer was used to determine mitochondrial function in all of the MCF7 transfected cell lines, after 48 hours of pre-treatment with 4-OHT (1 µM). FIG. 5A is a representative line graph of three independent experiments (+/− SEM), showing OCR over time. FIGS. 5B-5C show basal respiration, maximal respiration, and ATP production, respectively. Respiration (basal and maximal) and ATP levels were significantly increased in MCF7-Y537S and MCF7-Y537N cells. However, MCF7-Y537S cells showed the largest increases. For these data,  indicates $p<0.001$; ** indicates $p<0.00001$; ns indicates not significant.

Figure 6A:
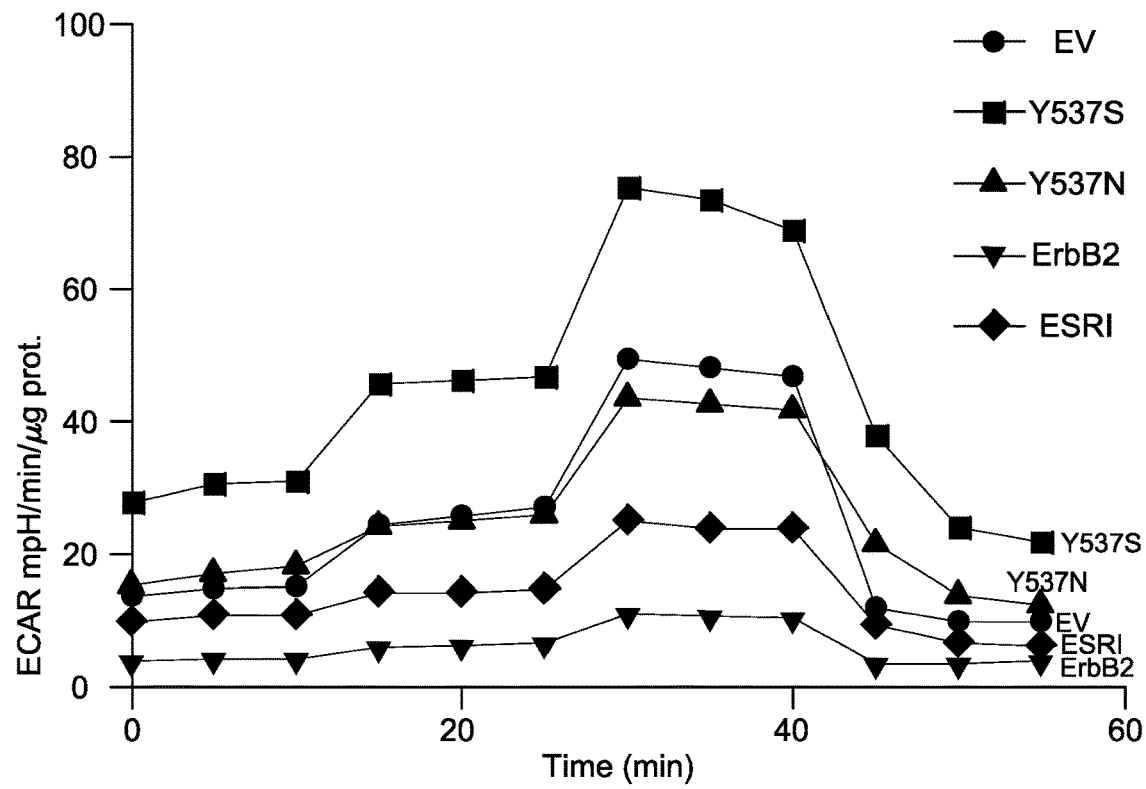
FIGS. 6A-6D show extracellular acidification rate (ECAR) and glycolysis level data in the transfected cell lines. Specifically.
Figure 6B:
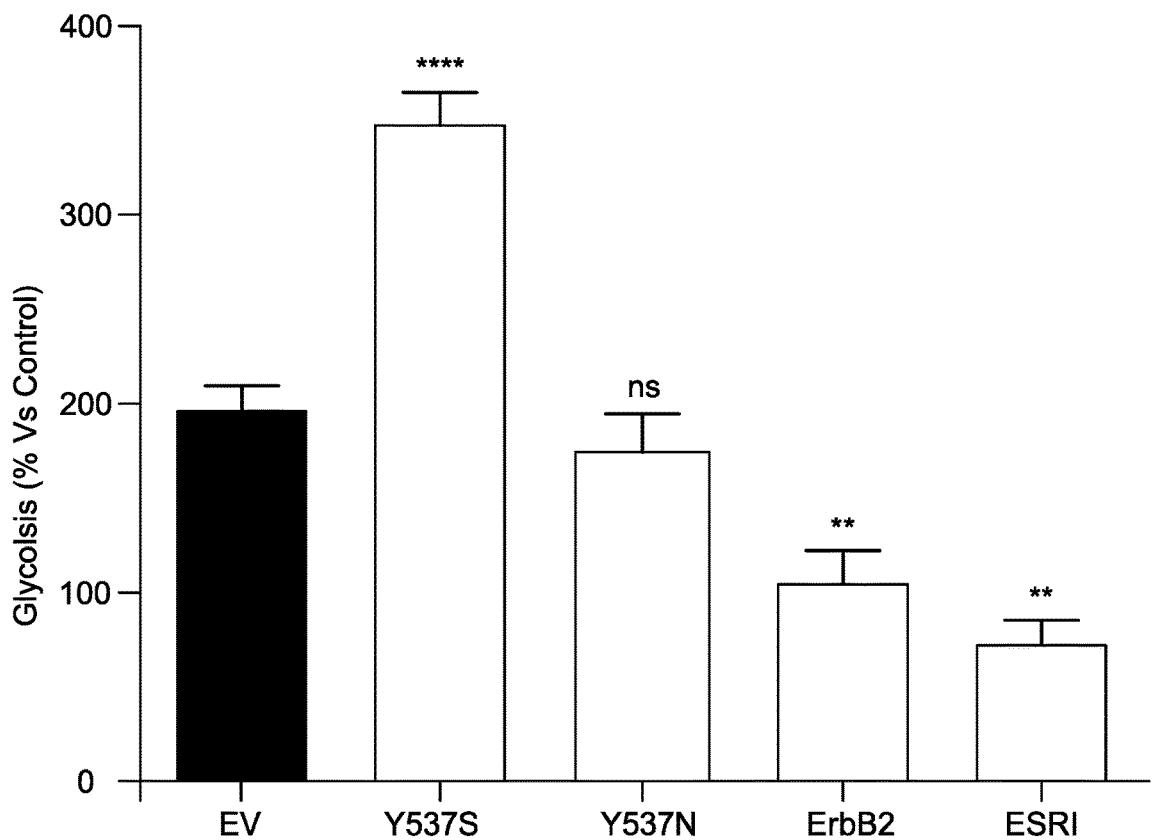
Figure 6C:
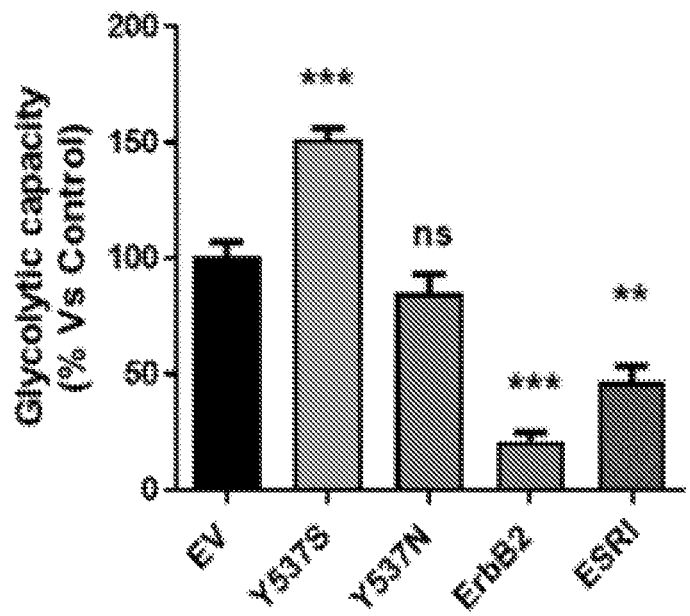
Figure 6D:
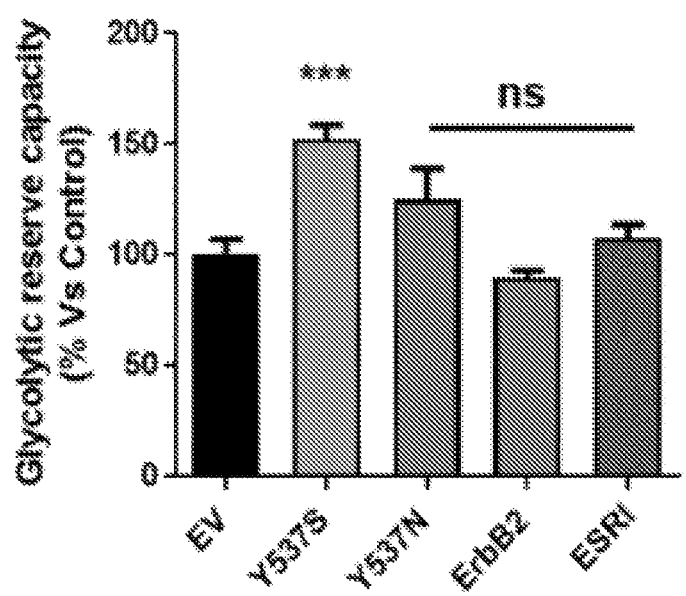

FIGS. 6A-6D show extracellular acidification rate (ECAR) and glycolysis level data in the transfected cell lines. Specifically, FIG. 6A shows ECAR over a one-hour time, and FIGS. 6B-6D show glycolysis, glycolytic capacity, and glycolytic reserve capacity, respectfully. The glycolysis data is presented as a percent relative to the control (EV). For these data, a Seahorse XFe96 metabolic-flux analyzer was employed to determine the metabolic function of all transfected cells after 48 hours of treatment with 4-OHT (1 µM). The data in FIG. 6A is a representative line graph of 3 independent experiments (+/− SEM). As can be seen in FIG. 6B, glycolysis was significantly increased only in the MCF7-Y537S cells, whereas MCF7-ErbB2 and MCF7-ESR1 cells showed decreased glycolysis. Glycolytic capacity was significantly increased only in MCF7-Y537S, and reduced in MCF7-ErbB2 and MCF7-ESR1 cells, as shown by FIG. 6C. Similarly, FIG. 6D shows that glycolytic reserve capacity was significantly increased only in MCF7-Y537S cells. For these data,  indicates $p<0.001$; * indicates $p<0.0001$; **** indicates $p<0.00001$; and ns indicates not significant The data show that the Y537S mutation significantly increases the mitochondrial OCR and ATP production, by >3-fold and ~2-fold, respectively. Similarly, the Y537S mutation also substantially elevated glycolysis and the glycolytic reserve capacity, by nearly 2-fold. Therefore, MCF7-Y537S cells are hyper-metabolic, with enhanced mitochondrial and glycolytic function.

Figure 7A:
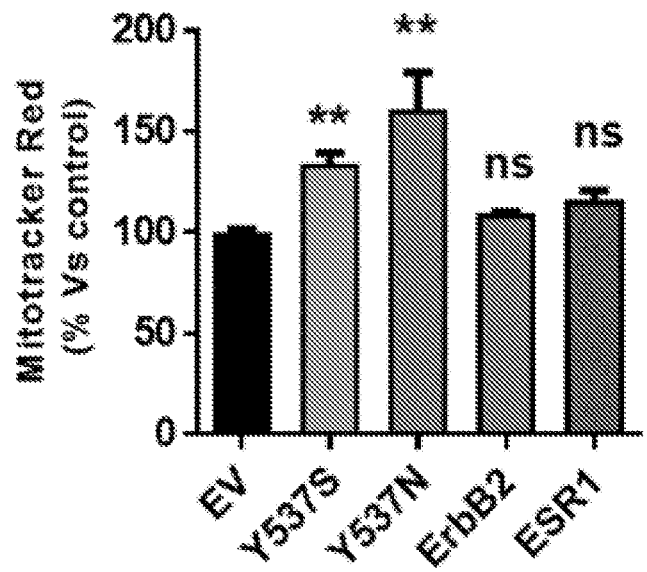
FIGS. 7A-7C show mitochondrial biogenesis and membrane potential data for the transfected MCF7 transfected cells.
Figure 7B:
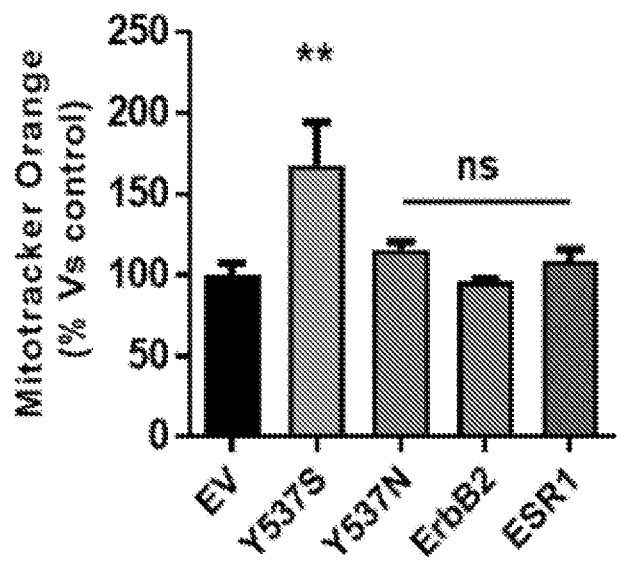
Figure 7C:
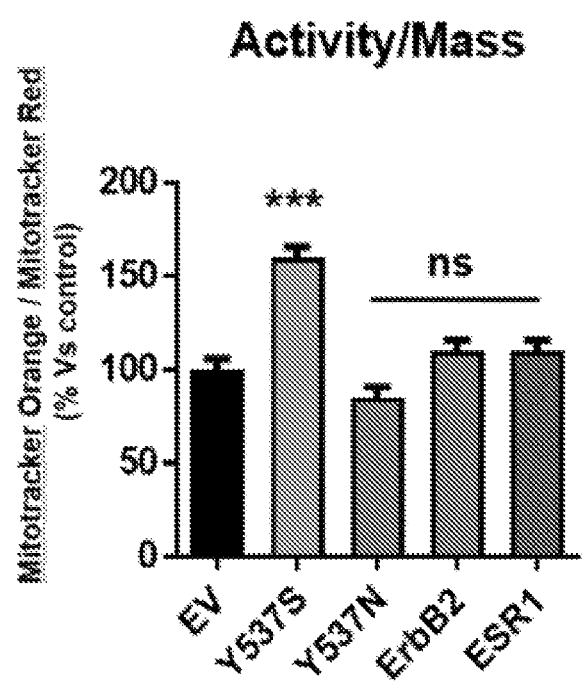

The elevated mitochondrial function is due to increased mitochondrial biogenesis. FIGS. 7A-7C show mitochondrial biogenesis and membrane potential data for the transfected MCF7 cells in the presence of 4-OHT, as observed by flow-cytometry with MitoTracker probes. This data was collected by first subjecting MCF7-Y537S cells to flow-cytometry, using MitoTracker probes. FACS analysis was carried out on MCF7 transfected cells after pre-treatment with 4-OHT. FIG. 7A shows MitoTracker Red and FIG. 7B shows data for MitoTracker Orange, both as a percentage of the EV control. Note that MCF7-Y537S and MCF7-Y537SN cells show a significant increase in mitochondrial mass (MitoTracker Red), but an increased mitochondrial membrane potential (MitoTracker Orange) was observed only in MCF7-Y537S in growth media with 4-OHT (1 µM). The data is also useful for calculating the activity/mass ratio, which was also increased in MCF7-Y537S cells. FIG. 7C shows the ratio (activity/mass) of mitochondrial membrane potential (MitoTracker Orange) and mitochondrial mass (MitoTracker Red), which was increased only in MCF7-Y537S cells, in growth media containing 4-OHT. For these data,  indicates $p<0.001$; * indicates $p<0.0001$; ns=not significant.

The MCF7-Y537S data indicates remarkably similar behavior with TAMR cells. Previous studies with TAMR cells reported similar metabolic re-programming, with increased OCR and ATP production, as well as elevated mitochondrial biogenesis. TAMR cells are an MCF7-based model of Tamoxifen-resistance, generated via the long-term culture of MCF7 cells in the presence of increasing concentrations of Tamoxifen.

Proteomics analysis reveals that the Y537S mutation up-regulates key metabolic targets and hyper-activates Rho-GDI/PTEN signaling in MCF7 cells. The hyper-metabolic phenotype observed via Seahorse analysis was validated by subjecting MCF7-Y537S cells to unbiased label-free proteomics analysis. For example, MCF7-Y537S cells were compared to MCF7-ESR1(WT) and empty-vector alone control cells, all in the presence of Tamoxifen.

Relative to ESR1(WT), the ESR1(Y537S) mutant showed dramatic increases in 33 mitochondrial proteins, consistent with increased mitochondrial oxygen consumption (OXPHOS) and elevated mitochondrial biogenesis. Table 1, below, shows up-regulation of mitochondrial-related proteins induced by the ESR1 (Y537S) mutant, using ESR1-WT as the comparison. Proteins in bold with an asterisk indicate proteins involved with mitochondrial biogenesis. It should be appreciated that these proteins may be used as biomarkers prognostic of resistance to endocrine therapies, such as Tamoxifen. They may also be used in conjunction with one or more of the up-regulated proteins from Table 2, and/or one or more of the up-regulated signaling molecules identified in Table 3.

TABLE 1

Mitochondrial-related proteins induced by the ESR1 (Y537S) mutant, as compared with ESR1-WT.

| Symbol | Description | Fold-Change (Up-regulation) |
|---|---|---|
| UQCRC2* | Cytochrome b-c1 complex subunit 2, mitochondrial | 110.11 |
| HIBADH | 3-hydroxyisobutyrate dehydrogenase, mitochondrial | 54.89 |
| NDUFB10* | NADH dehydrogenase [ubiquinone] 1 beta subcomplex subunit | 49.59 |
| PGAM5 | Serine/threonine-protein phosphatase PGAM5, mitochondrial | 8.8 |
| MRPL47* | 39S ribosomal protein L47, mitochondrial | 8.27 |
| ACSS1 | Acetyl-coenzyme A synthetase 2-like, mitochondrial | 7.15 |
| FH | Fumarate hydratase, mitochondrial | 6.68 |
| HSPD1* | 60 kDa heat shock protein, mitochondrial | 6.02 |
| OGDH | 2-oxoglutarate dehydrogenase E1 component, mitochondrial | 5.44 |
| MRPL4* | 39S ribosomal protein L4, mitochondrial | 4.54 |
| GRPEL1* | GrpE protein homolog 1, mitochondrial | 4.48 |
| ISOC2 | Isochorismatase domain-containing protein 2, mitochondrial | 3.8 |
| DUT | Deoxyuridine 5'-triphosphate nucleotidohydrolase, mitochondrial | 2.93 |
| **SDHB *** | Succinate dehydrogenase [ubiquinone] iron-sulfur subunit, mitochondrial | 2.75 |
| NDUFV1* | NADH dehydrogenase [ubiquinone] flavoprotein 1, mitochondrial | 2.74 |
| ECSIT | Evolutionarily conserved signaling intermediate in Toll pathway, mitochondrial | 2.7 |
| **GATC *** | Glutamyl-tRNA(Gln) amidotransferase subunit C, mitochondrial | 2.68 |
| PTRH2* | Peptidyl-tRNA hydrolase 2, mitochondrial | 2.35 |
| DNAJA3* | DnaJ homolog subfamily A member 3, mitochondrial | 2.14 |
| AKAP1* | A-kinase anchor protein 1, mitochondrial | 2.07 |
| HSPA9* | Stress-70 protein, mitochondrial | 2.04 |
| FDXR* | NADPH: adrenodoxin oxidoreductase, mitochondrial | 1.99 |
| TIMM23B* | Putative mitochondrial import inner membrane translocase subunit Tim23B | 1.95 |
| COX4/1* | Cytochrome c oxidase subunit 4 isoform 1, mitochondrial | 1.94 |
| NDUFA5* | NADH dehydrogenase [ubiquinone] 1 alpha subcomplex subunit 5 | 1.93 |
| CLUH* | Clustered mitochondria protein homolog | 1.88 |
| GLS | Glutaminase kidney isoform, mitochondrial | 1.85 |
| ABCB6* | ATP-binding cassette sub-family B member 6, mitochondrial | 1.85 |
| PPA2 | Inorganic pyrophosphatase 2, mitochondrial | 1.83 |
| MRPL43* | 39S ribosomal protein L43, mitochondrial | 1.7 |
| MRPS16* | 28S ribosomal protein S16, mitochondrial | 1.69 |
| MRPL15* | 39S ribosomal protein L15, mitochondrial | 1.64 |
| MRPS18B* | 28S ribosomal protein S18B, mitochondrial | 1.6 |

In addition, the ESR1 (Y537S) mutant also showed significant elevations in glycolytic and PPP enzymes. Table 2, below, shows the data. TIGAR, which has been previously shown to be sufficient to confer Tamoxifen-resistance, had a near-infinite up-regulation. However, TIGAR has not, until now, been recognized as having prognostic value of endocrine therapy resistance. It should be appreciated that these enzymes, alone or in combination, may be used as biomarkers prognostic of resistance to endocrine therapies, such as Tamoxifen due to the Y537S mutation. They may also be used in conjunction with one or more of the up-regulated proteins from Table 1, and/or one or more of the up-regulated signaling molecules identified in Table 3.

TABLE 2

Glycolysis and PPP-related proteins induced by the ESR1 (Y537S) mutant, as compared with ESR1-WT.

| Symbol | Description | Fold-Change (Up-regulation) |
|---|---|---|
| TIGAR | Fructose-2,6-bisphosphatase (TIGAR) | Infinity |
| ENO2 | Gamma-enolase | 128.23 |
| GAPDH | Glyceraldehyde-3-phosphate dehydrogenase | 7.41 |
| PKM | Pyruvate kinase | 7.41 |
| PHGDHL1 | Phosphoglycerate dehydrogenase like 1 | 4.51 |
| PFKP | Phosphofructokinase, platelet | 3.08 |
| ENO1 | Enolase | 3.07 |
| TALDO1 | Transaldolase | 2.3 |
| G6PD | Glucose-6-phosphate 1-dehydrogenase | 2.19 |

Additionally, the ESR1 (Y537S) mutant was specifically associated with high levels of seven markers of poor clinical outcome: COL6A3, ERBB2, STAT5, AFP, TFF1, CDK4, CD44. Table 3 shows the key signaling molecules induced by the ESR1 (Y537S) mutant, as compared with ESR1-WT. The proteomics data demonstrates that a single point mutation in the estrogen receptor can drive extensive metabolic re-programming, resulting in a hyper-metabolic phenotype. It should be appreciated that these enzymes, alone or in combination, may be used as biomarkers prognostic of resistance to endocrine therapies, such as Tamoxifen, due to the Y537S mutation. They may also be used in conjunction with one or more of the up-regulated proteins from Table 1 and Table 2.

TABLE 3

Key signaling molecules induced by the ESR1 (Y537S) mutant, as compared with ESR1-WT.

| Symbol | Description | Fold-Change (Up-regulation) |
|---|---|---|
| COL6A3 | Collagen, type VI, alpha 3 | Infinity |
| ERBB2 | Erb-b2 avian erythroblastic leukemia viral oncoprotein 2 | 14,233.50 |
| STAT3 | Signal transducer and activator of transcription 3 | 28.56 |
| AFP | Alpha-fetoprotein | 12.07 |
| TFF1 | Trefoil factor 1 | 3.92 |
| CDK4 | Cyclin-dependent kinase 4, isoform | 2.82 |
| CD44 | CD44 antigen | 1.98 |

Figure 8:
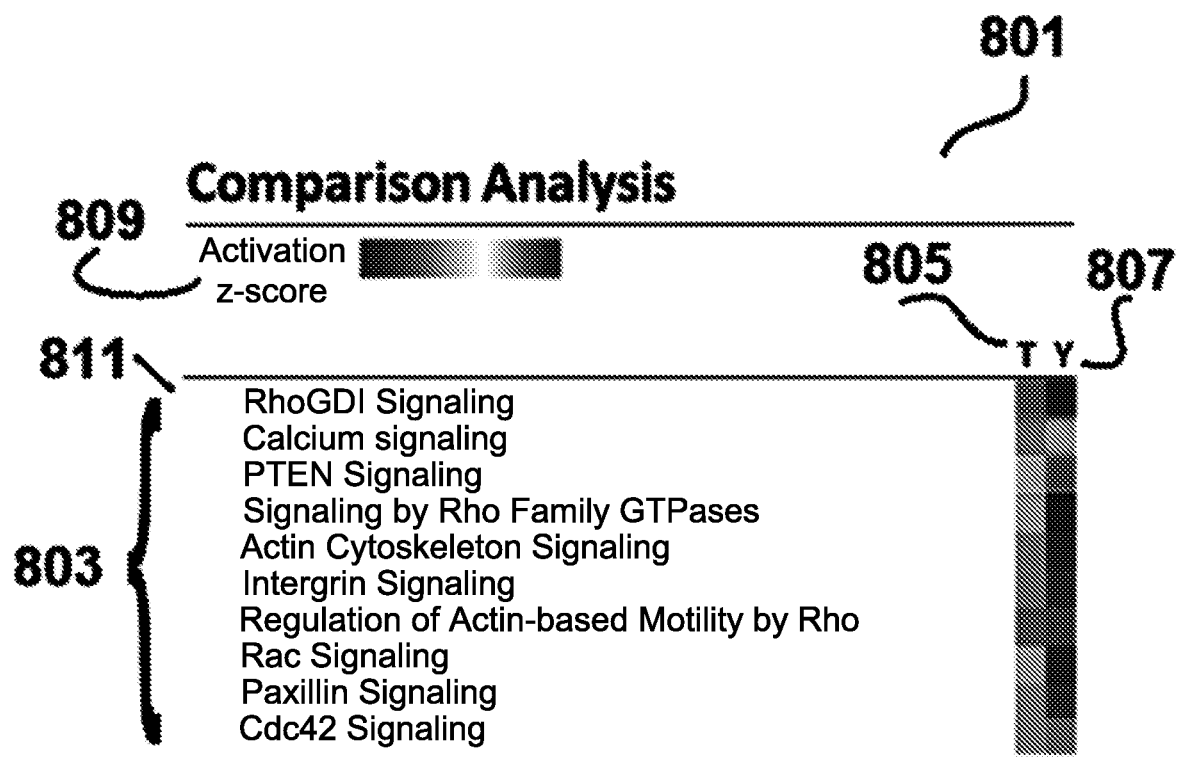
FIG. 8 compares HeatMaps for the top ten regulated canonical signaling pathways for Tamoxifen-resistant breast cancer cell lines and the MCF7-Y537S transfected cells.

FIG. 8 compares HeatMaps for the top ten regulated canonical signaling pathways for Tamoxifen-resistant breast cancer cell lines MCF7-TAMR and the MCF7-Y537S transfected cells. The Ingenuity Pathway Analysis of proteomics data sets shown in FIG. 8 compares MCF7-TAMR cells to MCF7-Y537S cells. The canonical signaling pathways predicted to be altered are shown, using MCF7 control cells. Each cell set was grown as a monolayer. HeatMaps 801 of the top 10 regulated canonical pathways listed in the left column 803, the activation score 805 for MCF7-TAMR cells in the column headed T, and the activation score 807 for MCF7-Y537S cells in the column headed Y. Legend 809 above shows a positive z-score (right-most) that indicates the activation of a signaling pathway, and a negative z-score (left-most) that indicates the inhibition of a signaling pathway. For this data, p<0.05 and cutoff z-score±2. These extensive comparisons revealed that a Rho-GDI/PTEN signaling pathway 911, the first listed pathway, appears to be hyper-activated in both of the Tamoxifen-resistant cell lines.

The metabolic targets identified in MCF7-Y537S cells were also transcriptionally upregulated in human breast cancer cells in vivo. A published clinical data set of N=28 breast cancer patients in which their tumor samples were subjected to laser-capture micro-dissection (25), to physically separate epithelial cancer cells from their adjacent tumor stroma. Table 4 presents a summary of these findings. Transcriptional profiling data derived from the analysis of N=28 breast cancer patients are shown in Table 4, highlighting the levels of fold-upregulation observed in the epithelial cancer cell compartment (relative to the tumor stroma), and corresponding p-values derived from the analysis of these clinical samples. Overall, many of the metabolic targets identified above were also transcriptionally elevated in human breast cancer cells in vivo.

TABLE 4

ESR1 (Y537S) targets are transcriptionally up-regulated in human breast cancer cells in vivo (Cancer Epithelia vs. Tumor Stroma).

| Symbol | Gene Description | Up-regulation (Fold-Change) | P-value |
|---|---|---|---|
| Mitochondrial components | | | |
| FH | Fumarate hydratase, mitochondrial | 5.42 | 7.06E−07 |
| UQCRC2 | Cytochrome b-c1 complex subunit 2, mitochondrial | 4.84 | 5.73E−06 |
| SDHB | Succinate dehydrogenase [ubiquinone] iron-sulfur subunit, mitochondrial | 4.25 | 4.24E−05 |
| HSPA9 | Stress-70 protein, mitochondrial | 3.69 | 2.64E−04 |
| MRPS18B | 28S ribosomal protein S18B, mitochondrial | 3.65 | 2.94E−04 |
| HSPD1 | 60 kDa heat shock protein, mitochondrial | 3.42 | 5.93E−04 |
| COX4I1 | Cytochrome c oxidase subunit 4 isoform 1, mitochondrial | 3.39 | 6.61E−04 |
| AKAP1 | A-kinase anchor protein 1, mitochondrial | 3.33 | 7.75E−04 |
| PPA2 | Inorganic pyrophosphatase 2, mitochondrial | 3.19 | 1.17E−03 |
| DNAJA3 | DnaJ homolog subfamily A member 3, mitochondrial | 2.92 | 2.57E−03 |
| PTRH2 | Peptidyl-tRNA hydrolase 2, mitochondrial | 2.77 | 3.82E−03 |
| NDUFA5 | NADH dehydrogenase [ubiquinone] 1 alpha subcomplex subunit 5 | 2.75 | 4.07E−03 |
| GRPEL1 | GrpE protein homolog 1, mitochondrial | 2.39 | 1.01E−02 |
| MRPL15 | 39S ribosomal protein L15, mitochondrial | 2.26 | 1.39E−02 |
| DUT | Deoxyuridine 5'-triphosphate nucleotidohydrolase, mitochondrial | 1.87 | 3.37E−02 |
| GLS | Glutaminase kidney isoform, mitochondrial | 1.81 | 3.81E−02 |
| Glycolytic/PPP enzymes | | | |
| TALDO1 | Transaldolase | 4.13 | 6.35E−05 |
| PKM2 | Pyruvate kinase 2 | 3.26 | 9.79E−04 |
| GAPDH | Glyceraldehyde-3-phosphate dehydrogenase | 2.97 | 2.22E−03 |
| ENO1 | Enolase | 1.96 | 2.75E−02 |
| Cell signalling molecules | | | |
| CD44 | CD44 antigen | 3.44 | 5.69E−04 |
| CDK4 | Cyclin-dependent kinase 4, isoform | 2.33 | 1.19E−02 |
| TFF1 | Trefoil factor 1 | 1.76 | 4.17E−02 |

Certain metabolic proteins up-regulated by the Y537S mutation in MCF7 cells have clinical prognostic value for predicting the onset of Tamoxifen-resistance (or other endocrine therapy resistance) in breast cancer patients. The mRNA expression levels in a cohort of ER(+)-patients was used to identify the up-regulated proteins having prognostic value. The population consisted of 152 patients, with the most common sub-type of breast cancer (Luminal A), with local lymph-node (LN) metastasis at diagnosis, specifically undergoing endocrine therapy (mostly Tamoxifen), without any form of chemotherapy. In such a setting, Tamoxifen-resistance manifests itself clinically, as either i) tumor recurrence or ii) distant metastasis. As such, Kaplan-Meier (K-M) curves were constructed using recurrence-free survival (RFS) or distant-metastasis free survival (DMFS), over a period of 10 to 15 years of follow-up. Hazard-ratios (HR) and p-values (log-rank test) were calculated and are as shown in Tables 5-8 below. In these tables, RFS refers to recurrence-free survival, and DMFS refers to distant metastasis-free survival. It should be appreciated that the genes identified in Tables 5-8 are prognostic of resistance to endocrine therapy, distant metastasis, and tumor recurrence, and may be used as biomarkers individually or in combination. Also, as discussed below, these biomarkers may be used to identify patients for receiving one or more mitochondrial biogenesis inhibitor therapies, to reduce and/or eliminate the resistance, and/or to increase the effectiveness of the endocrine therapy.

TABLE 5

Mitochondrial-related proteins induced by the ESR1 (Y537S) mutant: Association with Tumor Recurrence.

| Symbol | Probe | RFS-HR (Hazard Ratio) | Log-Rank Test |
|---|---|---|---|
| HSPD1 | 200807_s_at | 3.4 | 1.20E−05 |
| HSPD1 | 200806_s_at | 2.36 | 0.0035 |
| MRPL15 | 218027_at | 3.2 | 1.70E−05 |
| MRPL4 | 218105_s_at | 2.2 | 0.005 |
| AKAP1 | 210626_at | 2.19 | 0.007 |
| AKAP1 | 201674_s_at | 1.9 | 0.025 |
| PTRH2 | 218732_at | 2.17 | 0.005 |
| COX4I1 | 202698_x_at | 2.04 | 0.049 |
| GRPEL1 | 212434_at | 2.01 | 0.012 |
| HSPA9 | 200691_s_at | 1.97 | 0.024 |
| MRPS16 | 218046_s_at | 1.96 | 0.015 |

TABLE 6

Glycolysis and PPP-related proteins induced by the ESR1 (Y537S) mutant: Association with Tumor Recurrence.

| Symbol | Probe | RFS-HR (Hazard Ratio) | Log-Rank Test |
|---|---|---|---|
| ENO1 | 201231_s_at | 2.28 | 0.004 |
| TALDO1 | 201463_s_at | 2.14 | 0.014 |
| TIGAR | 219099_at | 2.13 | 0.008 |
| ENO2 | 201313_at | 1.92 | 0.019 |

TABLE 7

Mitochondrial-related proteins induced by the ESR1 (Y537S) mutant: Association with Distant Metastasis.

| Symbol | Probe | DMFS-HR (Hazard Ratio) | Log-Rank Test |
|---|---|---|---|
| HSPD1 | 200807_s_at | 3.47 | 9.00E−05 |
| HSPD1 | 200806_s_at | 2.03 | 0.03 |
| GRPEL1 | 212434_at | 3.18 | 0.004 |
| MRPL15 | 218027_at | 2.57 | 0.0035 |
| MRPS16 | 218046_s_at | 2.53 | 0.006 |
| COX4I1 | 202698_x_at | 2.26 | 0.013 |

TABLE 8

Glycolysis-related proteins induced by the ESR1 (Y537S) mutant: Association with Distant Metastasis.

| Symbol | Probe | DMFS-HR (Hazard Ratio) | Log-Rank Test |
|---|---|---|---|
| ENO2 | 201313_at | 2.7 | 0.0035 |
| ENO1 | 201231_s_at | 2.29 | 0.01 |

More specifically, Tables 5 and 7 highlight the mitochondrial mRNA transcripts associated with tumor recurrence and distant metastasis, respectively. Similarly, Tables 6 and 8 show the glycolytic and PPP enzyme mRNA transcripts associated with poor clinical outcomes. The mRNA levels of key metabolic proteins induced by the Y537S mutation positively predict treatment failure during endocrine therapy, highlighting their clinical relevance. These findings provide a direct functional link between the Y537S mutation, metabolic re-programming and the clinical response to endocrine therapy.

It should be appreciated that one or more of the proteins identified in Tables 5-8 may be used as a biomarker having prognostic value of endocrine therapy failure. Certain metabolic proteins were up-regulated in both tumor-recurrence and distant metastasis data sets, indicating increased prognostic value of endocrine therapy treatment failure. These metabolic proteins include mitochondrial-related proteins HSPD1, GRPEL1, MRPL15, MRPS16, and COX4I1, and glycolysis proteins ENO1 and ENO2.

The Y537S mutation is linked to TIGAR (TP53-inducible glycolysis and apoptosis regulator). TIGAR was originally discovered as a p53-regulated gene. However, TIGAR shows striking protein sequence similarity to the glycolytic enzyme that degrades fructose-2,6-bisphosphate, especially within its bisphosphate domain. Therefore, TIGAR likely functions as an inhibitor of glycolysis, but also stimulates the up-regulation of the pentose-phosphate pathway (PPP) and can confer protection against apoptosis. Expression of TIGAR is sufficient to confer Tamoxifen-resistance. The expression of TIGAR is infinitely up-regulated by expression of the Y537S mutation, which helps explain the mechanism by which Y537S confers Tamoxifen-resistance, namely the hyper-metabolic phenotype and the avoidance of apoptosis.

The Y537S mutation is associated with COL6A3, a gene providing instructions for making a component of type VI collagen. Collagen VI is an extracellular matrix protein that has been previously associated with tumor progression and distant metastasis. The expression of COL6A3 is infinitely up-regulated by expression of the Y537S mutation, which also explains the mechanism by which Y537S confers Tamoxifen-resistance. Tumor-specific isoforms of COL6A3 have been reported.

Marker proteins induced by the Y537S mutation are prognostic of the response to endocrine therapy. Certain metabolic proteins up-regulated by the Y537S mutation in MCF7 cells have clinical prognostic value for predicting the onset of Tamoxifen-resistance in breast cancer patients (i.e., tumor recurrence and/or distant metastasis). Biomarkers prognostic of tumor recurrence include mitochondrial-related proteins HSPD1, MRPL15, MRPL4, AKAP1, PTRH2, COX4I1, GRPEL1, HSPA9, MRPS16, and glycolysis and PPP-related proteins ENO1, TALD01, TIGAR, ENO2. Biomarkers prognostic of distant metastasis include mitochondrial-related proteins HSPD1, GRPEL1, MRPL15, MRPS16, COX4I1, and glycolysis-related proteins ENO2, ENO1. Importantly, the results indicate that the mRNA levels of key metabolic proteins induced by the Y537S mutation positively predict treatment failure during endocrine therapy, highlighting their clinical relevance. Certain biomarkers are prognostic of both tumor recurrence and distant metastasis: mitochondrial-related proteins HSPD1, GRPEL1, MRPL15, MRPS16, and COX4I1, and glycolysis proteins ENO1 and ENO2. These findings provide a direct functional link between the Y537S mutation, metabolic re-programming and the clinical response to endocrine therapy, and also provide valuable diagnostic tools for identifying Tamoxifen-resistant tumor cells, as well as tumors that may be advantageously treated with one or more mitochondrial biogenesis inhibitors to reduce or eliminate Tamoxifen resistance, distant metastasis, and tumor recurrence.

In addition to the identified biomarkers prognostic of Tamoxifen-resistance, this disclosure addresses therapeutics for reducing or eliminating Tamoxifen resistance, as well as the risk of tumor recurrence and distant metastasis. Under the present approach, one or more inhibitors of mitochondrial biogenesis may be used to reduce or eliminate Tamoxifen resistance. In some embodiments, at least one mitochondrial biogenesis inhibitor may be administered if one or more biomarkers prognostic of endocrine treatment failure is elevated relative to a threshold. In some embodiments, for example, Tamoxifen resistance may be reduced or eliminated by administering a pharmaceutically effective amount of at least one mitochondrial biogenesis inhibitor selected from: tetracycline, doxycycline, tigecycline, minocycline, eyrthromycin, azithromycin, clarithromycin, pyrvinium pamoate, atovaquone, bedaquiline, irinotecan, sorafenib, niclosamide, berberine, stiripentol, chloroquine, etomoxir, perhexiline, a mitoriboscin, a mitoketoscin, a mitoflavoscin, a TPP-derivative, mDIVI1, caffeic acid phenyl ester, an antimitoscin, and a repurposcin. The following paragraphs describe various categories of mitochondrial biogenesis therapeutics that may be used in embodiments of the present approach in more detail. It should be appreciated that other mitochondrial biogenesis inhibitors may be used without deviating from the present approach.

A first category of such therapeutics are mitoriboscins, as described in International Application No. PCT/US2018/022403, filed Mar. 14, 2018, and incorporated by reference in its entirety. The incorporated reference includes data for select mitoriboscin compounds. Generally, mitoriboscins are mitochondrial inhibitor compounds that have anti-cancer and often antimicrobial activity, chemotherapy-sensitizing, radiosensitizing, and photosensitizing effects, as well as anti-aging effects. These compounds bind to either the large sub-unit or the small sub-unit of the mitoribosome (or in some instances, both) and inhibit mitochondrial biogenesis.

Four groups of mitoriboscins (mitoribocyclines, mitoribomycins, mitoribosporins, and mitoribofloxins) are shown below. A mitoriboscin may be selected for use to reduce and/or eliminate Tamoxifen-resistance, as well as for anti-cancer, antibiotic, anti-aging therapeutics, among other uses. It should be appreciated by those skilled in the art that the therapeutically-effective amount of each compound, for a particular therapy, depends on a multitude of factors. In some embodiments, combinations of compounds from one or more mitoriboscin groups may be used, and in some embodiments other active ingredients may be used, such as other mitochondrial biogenesis inhibitors.

In some embodiments, the mitoriboscin compound may be a mitoribocycline having the general formula shown below, or salts thereof:

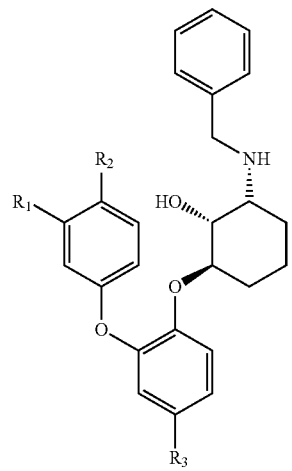

wherein each R1-R3 may be the same or different and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, benzoic acid-based derivatives, and one or more mitochondrial targeting signal. For clarification, mitochondrial targeting signals are any chemical or peptide entity that increases the efficiency of targeting the attached molecule to the mitochondria. Such modification would be expected to increase the potency and effectiveness of a mitoriboscin. Thus, R may be any mitochondrial targeting signal (peptide or chemical), including cationic compounds, such as tri-phenyl-phosphonium (TPP), a guanidinium-based moiety and/or choline esters, among others, including those discussed herein.

Demonstrative embodiments of mitoribocyclines include the following compounds:

Mitoriboscin Compound A

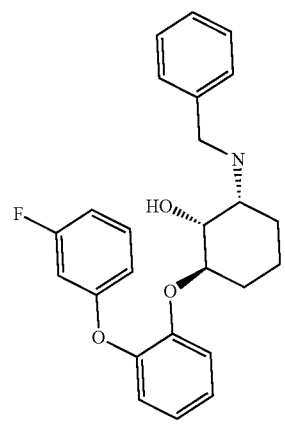

Mitoriboscin Compound B

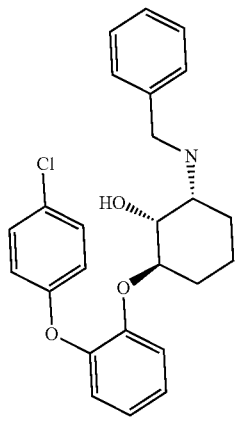

Mitoriboscin Compound C

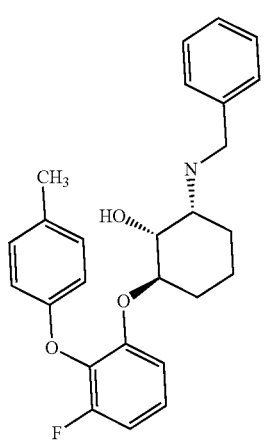

In some embodiments, the mitoriboscin compound may be a mitoribomycin having the general formula shown below, or salts thereof:

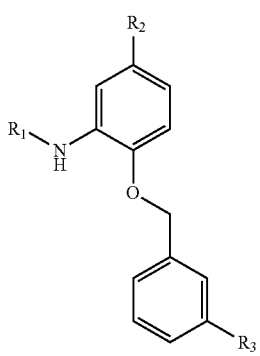

wherein each R may be the same or different and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, benzoic acid-based derivatives, and one or more mitochondrial targeting signals.

Demonstrative embodiments of mitoribocyclines in the mitoribomycin group include the following compounds:

Mitoriboscin Compound D

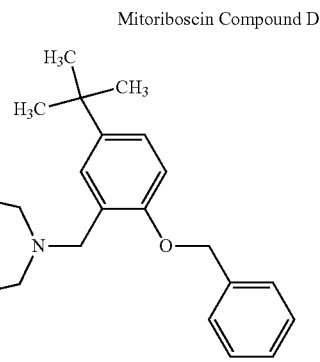

Mitoriboscin Compound E

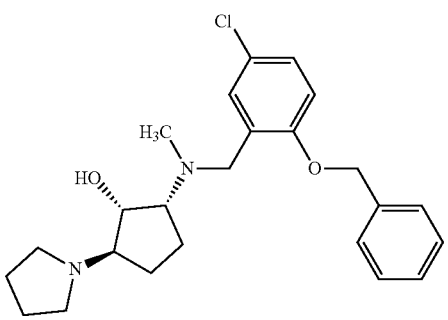

Mitoriboscin Compound F

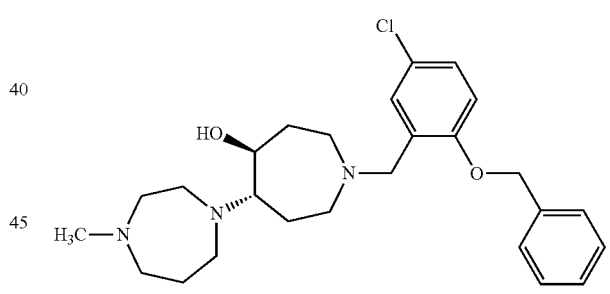

Mitoriboscin Compound G

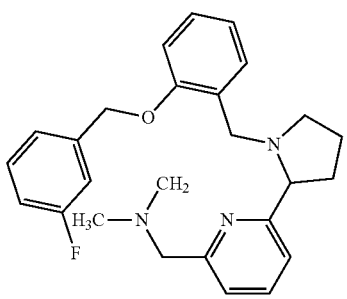

In some embodiments, the mitoriboscin compound may be a mitoribosporin having the general formula shown below, or salts thereof:

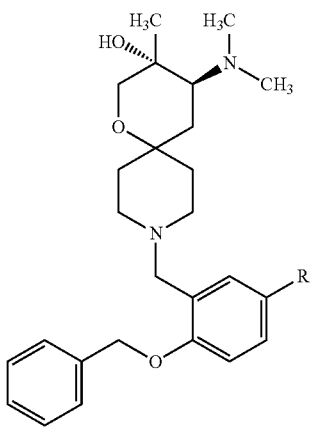

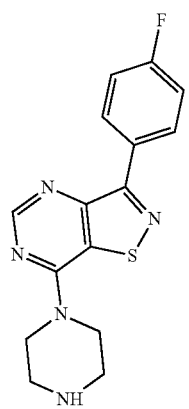

wherein R is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, benzoic acid-based derivatives, and one or more mitochondrial targeting signals.

Demonstrative embodiments of mitoribocyclines in the mitoribosporin group include the following compounds:

Mitoriboscin Compound H

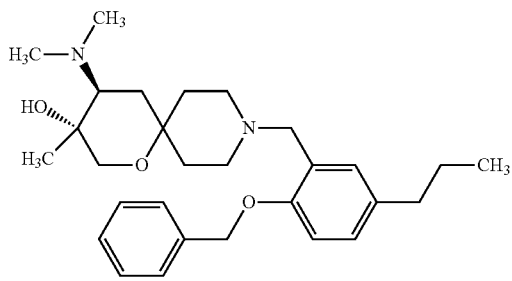

Mitoriboscin Compound I

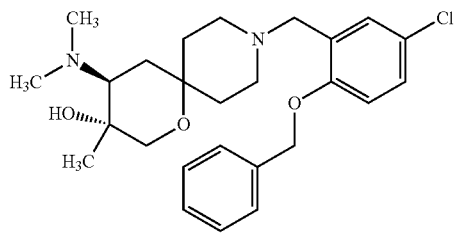

In some embodiments, the mitoriboscin compound comprises the formula or salts thereof:

It should be appreciated that the mitoriboscins may be selected for therapeutic use individually, or in combination with more than one specific mitoriboscin, and/or with other substances to enhance the efficacy of other therapeutics.

A second category of therapeutics include combination therapies involving oxidative metabolism inhibitors and glycolytic metabolism inhibitors. In some embodiments, Tamoxifen resistance may be reduced or eliminated by administering a pharmaceutically effective amount of at least one oxidative metabolism inhibitor, and at least one glycolytic metabolism inhibitor. Inhibitors of oxidative metabolism may include members of the tetracycline family and the erythromycin family. Members of the tetracycline family include tetracycline, doxycycline, tigecycline, minocycline, chlortetracycline, oxytetracycline, demeclocycline, lymecycline, meclocycline, methacycline, rolitetracycline, chlortetracycline, omadacycline, and sarecycline. Members of the erythromycin family include erythromycin, azithromycin, and clarithromycin. Glycolytic metabolism inhibitors may be selected from inhibitors of glycolysis, inhibitors of OXPHOS, and inhibitors of autophagy. Examples of glycolysis inhibitors include 2-deoxy-glucose, ascorbic acid, and stiripentol. OXPHOS inhibitors include atovaquone, irinotecan, sorafenib, niclosamide, and berberine chloride. Autophagy inhibitors include chloroquine. Table 9 provides examples of combinations. Data and further examples are described in International Application No. PCT/US2018/028587, filed Apr. 20, 2018, which is incorporated by reference in its entirety. In some embodiments, the mitochondrial biogenesis inhibitor comprises a combination of doxycycline, azithromycin, and ascorbic acid.

TABLE 9

Examples of combination therapies involving an oxidative metabolism inhibitor and at least one glycolytic metabolism inhibitor.

| Doxycycline Plus OXPHOS Inhibitor | Doxycycline Plus Glycolysis Inhibitor | Doxycycline Plus Autophagy Inhibitor |
|---|---|---|
| Atovaquone | 2-Deoxy-glucose (2-DG) | Chloroquine |
| Irinotecan | Ascorbic acid | |
| Sorafenib | Stiripentol | |
| Niclosamide | | |
| Berberine Chloride | | |

Some embodiments may take the form of a triple combination. For example, in some embodiments of the present approach, a first antibiotic inhibiting the large mitochondrial ribosome (such as, for example, members of the erythromycin family), and a second antibiotic inhibiting the small mitochondrial ribosome (such as, for example, members of the tetracycline family), may be administered with a pro-oxidant or an agent inducing mitochondrial oxidative stress (e.g., low concentrations of Vitamin C, radiation therapy, among other examples). As a specific example, FDA-approved antibiotics doxycycline and azithromycin may be used in connection with one or more common dietary supplements (e.g., Vitamin C). In an example embodiment, treatment with a combination of doxycycline (at 1 µM), azithromycin (at 1 µM), and Vitamin C (at 250 µM) may be used as the mitochondrial biogenesis inhibitor. The pro-oxidant may be, in some embodiments, a therapeutic agent having a pro-oxidant effect. For example, the pro-oxidant may be a therapeutic agent at a concentration that causes the therapeutic agent to act as a reducing agent. U.S. Provisional Patent Application 62/780,488, filed Dec. 17, 2018 and incorporated by reference in its entirety, provides further description of triple combination therapies.

A third category of mitochondrial biogenesis inhibitors, antimitoscins, is set forth in International Patent Application PCT/US2018/033466, filed May 18, 2018 and incorporated by reference in its entirety. Existing antibiotics having intrinsic anti-mitochondrial properties can be chemically modified to target the mitochondria and inhibit mitochondrial biogenesis. The term "antimitoscin" used herein broadly refers to an antibiotic having intrinsic anti-mitochondrial properties that is chemically modified to target the antibiotic to mitochondria. The contemporary art considers intrinsic anti-mitochondrial activity in antibiotics to be an unwanted side-effect. Indeed, some potential antibiotics have been excluded from trials due to excessive anti-mitochondrial properties, and researchers have viewed anti-mitochondrial activity as a potential drawback. However, under the present approach, an antibiotic's intrinsic anti-mitochondrial activity can become the basis for an entirely new therapeutic. The antimitoscin may be an antibiotic having intrinsic anti-mitochondrial properties chemically modified with a mitochondrial targeting signal (e.g., a chemical moiety). Chemical modification may be, for example, through covalent or non-covalent bonds. In some embodiments, the antibiotic is a member of the tetracycline family, the erthyromycin family, chloramphenicol, pyrvinium pamoate, atovaquone, and bedaquiline. The mitochondria-targeting signal may be at least one compound or moiety selected from the group comprising a membrane targeting signal and a mitochondrial ribosome-targeting signal. Examples of membrane targeting signals include palmitic acid, stearic acid, myristic acid, and oleic acid. Examples of mitochondrial ribosome-targeting signals include tri-phenyl-phosphonium (TPP) and guanidinium-based moieties. Other mitochondrial targeting signals are described below.

Examples of membrane targeting signals are shown below. It should be appreciated that other membrane targeting signals may be used, such as, for example, short-chain (e.g., fewer than 6 carbon atoms in the chain) fatty acids and medium-chain (e.g., 6-12 carbon atoms in the chain) fatty acids. A membrane targeting signal may be covalently or non-covalently bonded to the antibiotic for targeted delivery.

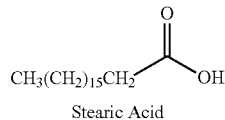
Stearic Acid

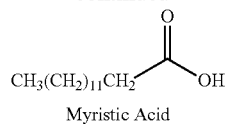
Myristic Acid

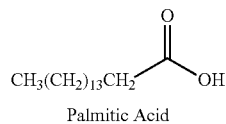
Palmitic Acid

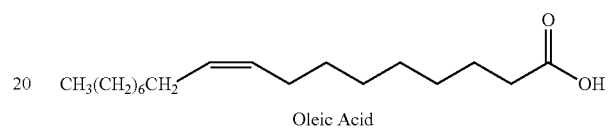
Oleic Acid

TPP and guanidinium are non-toxic chemical moieties that functionally behave as a mitochondrial targeting signal (MTS) in living cells. It may be bonded to an antibiotic, often through the use of a carbon spacer-arm or linking chain.

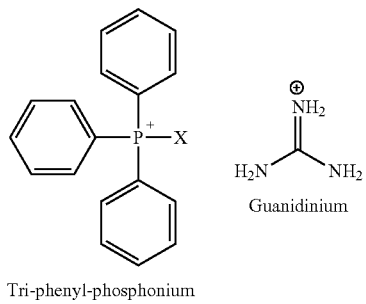
Tri-phenyl-phosphonium
Guanidinium

The examples below demonstrate the chemical modification of an antibiotic from the tetracycline family with a mitochondrial targeting signal. In the first example, the tetracycline family member is chemically modified with membrane targeting signal palmitic acid. In the second example, a carbon spacer arm $(CH_2)^n$ links TPP to the tetracycline family member. It should be appreciated that other binding locations may be used, and further that other mitochondrial targeting signals and antibiotics may be used without departing from the present approach.

Example 1

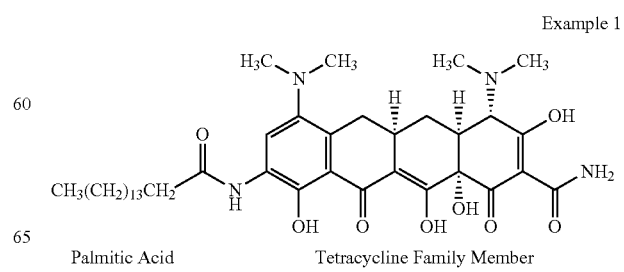
Palmitic Acid        Tetracycline Family Member

-continued

Example 2

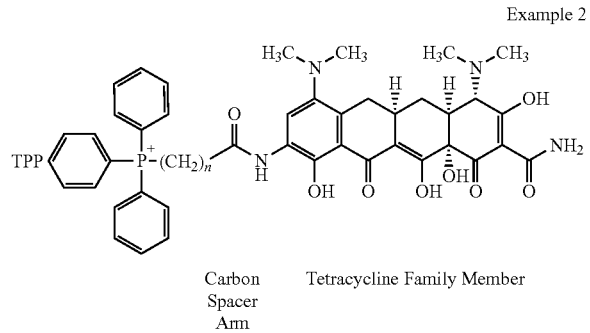

Carbon Spacer Arm     Tetracycline Family Member

A fourth category of mitochondria biogenesis inhibitors are mitoketoscins, non-carcinogenic compounds that bind to at least one of ACAT1/2 and OXCT1/2 and inhibit mitochondrial ATP production. These compounds are described more fully in International Application PCT/US2018/039354, filed Jun. 25, 2018, and incorporated by reference in its entirety. Generally, a mitoketoscin targets the mitochondrial enzymes responsible for ketone re-utilization and that have anti-cancer and antibiotic properties. These compounds bind to either or both active catalytic sites of OXCT1/2 and ACAT1/2 to inhibit mitochondrial function. Examples of mitoketoscins are general pharmacophore having the following structure (or salts thereof):

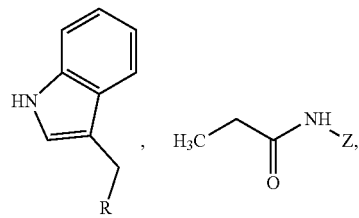

wherein Z is defined as ethylpiperidine or ethylpyrrolidine,

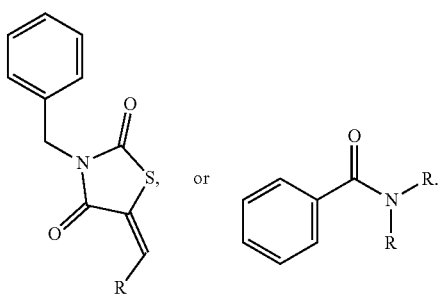

As another example, a mitoketoscin may be a general pharmacophore having one of the following structures (or salts thereof):

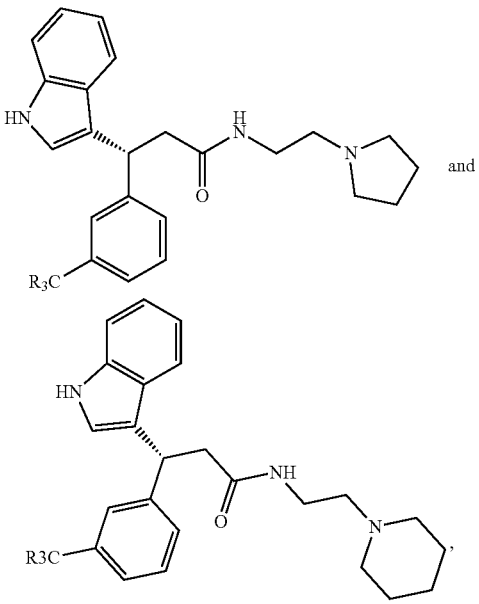

and wherein each R may be the same or different, and may be selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, and benzoic acid-based derivatives.

As a further example, a mitoketoscin may be a general pharmacophore having the following structure (or a salt thereof):

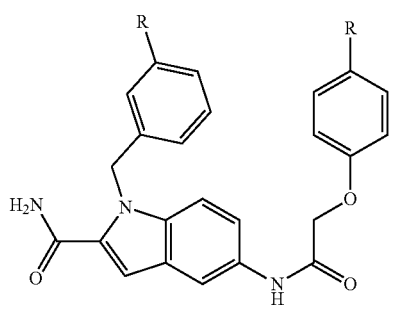

wherein each R may be the same or different and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polyclic arenes, heteroarenes, arene-based derivatives, heteroarene-based derivatives, phenols, phenol-based derivatives, benzoic acid, and benzoic acid-based derivatives.

As another example, a mitoketoscin may be a general pharmacophore having the following structure (or a salt thereof):

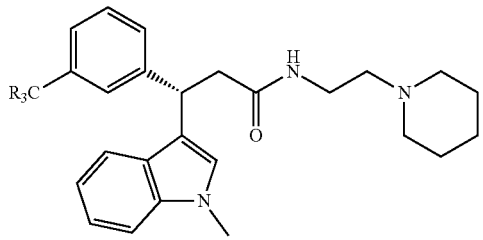

wherein each R may be the same or different and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, and benzoic acid-based derivatives.

Further examples of mitoketoscins are general pharmacophores having any of the following structures (or salts thereof):

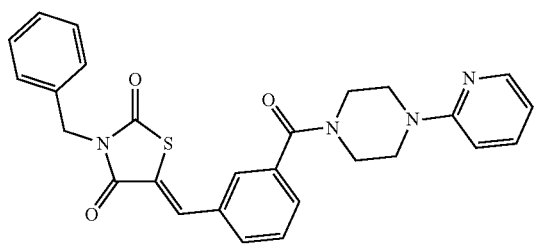 and

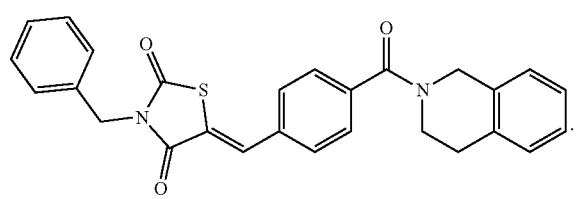

An additional example of a mitoketoscin is a general pharmacophore having the following structure (or a salt thereof):

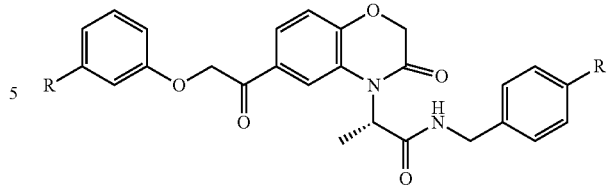

wherein each R may be the same or different and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, and benzoic acid-based derivatives.

Another example of a mitoketoscin is a general pharmacophore having the following structure (or a salt thereof):

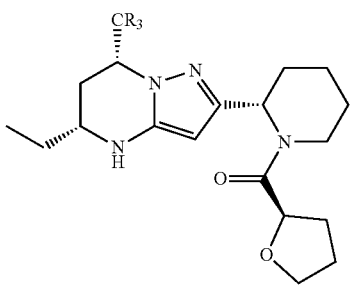

wherein each R may be the same or different and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, and benzoic acid-based derivatives.

A further example of a mitoketoscin is a general pharmacophore having the following structure (or a salt thereof):

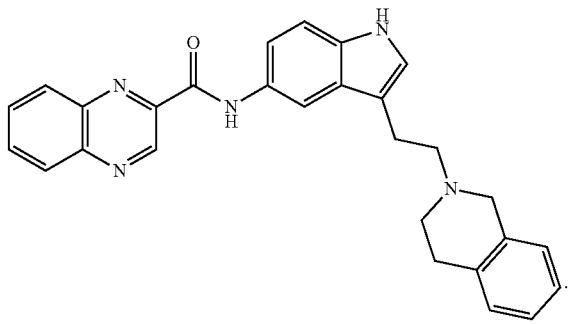 [SMILES: O=C(Nc1ccc2[nH]cc(CCN3CCc4ccccc4C3)c2c1)c1cnc2ccccc2n1]

Another example of a mitoketoscin is a general pharmacophore having the following structure (or a salt thereof):

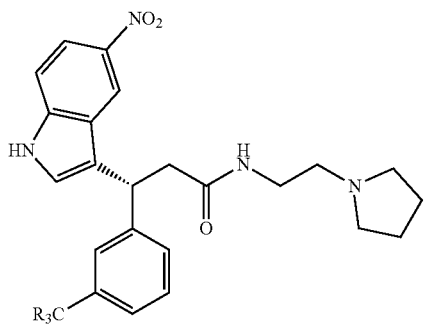

wherein each R may be the same or different and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, and benzoic acid-based derivatives. It should be appreciated that other mitoketoscins may be used without departing from the present approach. Further, it should be appreciated that a mitoketoscin may be modified with a mitochondrial targeting signal, such as discussed above with respect to antimitoscins.

Mitoflavoscins and mitoflavins are a fifth category of mitochondrial biogenesis inhibitors that may be used under the present approach. These compounds are described more fully in International Patent Application PCT/US2018/057093, filed Oct. 23, 2018 and incorporated by reference in its entirety. Mitoflavoscins are compounds that bind to flavin-containing enzymes and inhibit mitochondrial ATP production. Diphenyleneiodonium chloride (DPI) is an example of a mitoflavoscin. It should be appreciated that a mitoflavoscin may be modified with a mitochondrial targeting signal, such as discussed above with respect to antimitoscins. Mitoflavins, derivatives of riboflavin that inhibit mitochondrial function, may also be chemically modified with a mitochondrial targeting signal. For example, roseoflavin [8-Demethyl-8-(dimethylamino)-riboflavin or 8-Dimethylaminoriboflavin] is a naturally occurring anti-bacterial compound that is a derivative of riboflavin, which can be chemically modified to optimize its potential for targeting CSCs and inhibiting mitochondrial biogenesis. Lumichrome (7,8-Dimethylalloxazine) is a fluorescent photoproduct of riboflavin degradation, which also can be chemically modified to optimize its potential for targeting CSCs. Other common derivatives of riboflavin include: Alloxazine, Lumiflavine, 1,5-dihydroriboflavin and 1,5-dihydroflavin. Each of these riboflavin derivatives may be chemically modified with a mitochondrial targeting signal to form a mitoflavin, and may be used as a mitochondrial biogenesis inhibitor according to the present approach.

A sixth category of mitochondria biogenesis inhibitors is TPP-derivative compounds that show not only a strong preference for uptake in cancer cells (bulk cancer cells, cancer stem cells, and energetic cancer stem cells), but also disrupt mitochondrial biogenesis in these cells. These TPP-derivative compounds are described more fully in International patent Application PCT/US2018/062174, filed Nov. 21, 2018 and incorporated by reference in its entirety. As used with respect to TPP-derivatives, a derivative as known in the art is a compound that can be synthesized from a parent compound by replacing an atom with another atom or group of atoms. For example, a derivative of TPP is 2-butene-1,4-bis-TPP, which includes two phosphonium groups joined by butene. A derivative of 2-butene-1,4-bis-TPP, then, could include replacement of one or more phenyl groups with another compound, such as a halogen or an organic compound. For the sake of brevity, this disclosure does not identify all of the potential derivatives, as the description should be adequate for a person of ordinary skill in the art. Other examples of TPP-derivative compounds that may be used as mitochondrial biogenesis inhibitors according to the present approach include 2-butene-1,4-bis-TPP; derivatives of 2-butene-1,4-bis-TPP; 2-chlorobenzyl-TPP; derivatives of 2-chlorobenzyl-TPP; 3-methylbenzyl-TPP; derivatives of 3-methylbenzyl-TPP; 2,4-dichlorobenzyl-TPP; derivatives of 2,4-dichlorobenzyl-TPP; 1-naphthylmethyl-TPP; derivatives of 1-naphthylmethyl-TPP; p-xylylenebis-TPP; and derivatives of p-xylylenebis-TPP. Of course, it should be appreciated that the foregoing list is not an exhaustive list of TPP-derivatives.

Repurposcins are a seventh category of mitochondria biogenesis inhibitors that may be used in embodiments of the present approach. International Patent Application PCT/US2018/062956, filed Nov. 29, 2018 and incorporated by reference in its entirety, describes these compounds more fully. Generally, "repurposcins" are compounds having intrinsic anti-mitochondrial properties that are chemically modified to target the compounds to mitochondria. Such compounds may include, for example, FDA-approved pharmaceuticals, nutraceuticals, and supplements, among others. Compounds having intrinsic anti-mitochondrial properties may be chemically modified with one or more mitochondrial targeting signals as described above. Examples of compounds having intrinsic anti-mitochondrial properties include berberine chloride, quercetin, niclosamide, acriflavinium hydrochloride, sorafenib, emetine dihydrochloride, dactinomycin, plicamycin, suloctidil, teniposide, pentamidine isethionate, daunorubicin, thioguanine, amsacrine, phenformin hydrochloride, irinotecan hydrochloride, mitomycin, hydroxyprogesterone caproate, cyclosporine, lanatoside c, mercaptopurine, quinacrine hydrochloride, and fenofibrate. In some embodiments, the compound may be one or more of neomycin, puromycin, rapamycin (and its derivatives, such as everolimus), G418, trovafloxacin, levofloxacin, avocatin B, clarithromycin, ciprofloxacin, spiramycin, telithromycin, norfloxacin, moxifloxacin, ofloxacin, minocycline, tetracycline, demethylchlortetracycline, a member of the tetracycline family, a member the erthyromycin family, clindamycin, metronidazole, linezolid, mupirocin, vancomycin, clindamycin, cephalosporin, ciprofolxacin, streptomycin, amoxicillin, and azelaic acid. It should be noted that a repurposcin formed from an antibiotic may also be referred to as an antimitoscin.

An eighth category of mitochondrial biogenesis inhibitors that may be used in the present approach is MDIVI-1 derivatives, as described in International Patent Application PCT/US2018/066247, filed Dec. 18, 2018 and incorporated by reference in its entirety. Mitochondrial division inhibitor-1 (mDIVI-1) is a small molecule that selectively and reversibly inhibits DRP1. MDIVI-1 has been shown to target DRP1 by binding and suppressing both the DRP1 self-assembly into ring-like structures around the mitochondria and its capacity to catalyze GTP hydrolysis. The present approach may take the form of a mitochondrial fission inhibitor 1 (mDIVI-1) derivative having the general formula:

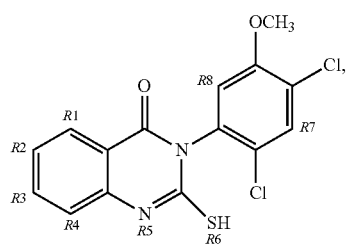

or a pharmaceutically acceptable salt thereof, wherein each of R1 through R8 may be selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivatives, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arenes, heteroarenes, arene-based derivatives, heteroarene-based derivatives, phenols, phenol-based derivatives, benzoic acid, benzoic acid-based derivatives, and a mitochondrial targeting signal. In some embodiments, at least one R-group is a mitochondrial targeting signal, such as palmitic acid, stearic acid, myristic acid, and oleic acid, a short-chain fatty acid, a medium-chain fatty acid, tri-phenyl-phosphonium (TPP), a TPP-derivative, a lipophilic cation, and 10-N-nonyl acridine orange. In some embodiments, at least one R-group is a mitochondrial targeting signal, such as one of 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP. It should be appreciated that MDIVI-1 derivatives may be used as mitochondrial biogenesis inhibitors under the present approach, with one or more of the chemical modifications described in this paragraph.

As described herein, under the present approach biomarkers having prognostic value of endocrine therapy failure may be used to identify cancer cells resistant to Tamoxifen or other endocrine therapeutics. These biomarkers may also be used to identify increased risks of distant metastasis and/or tumor recurrence. Biomarkers prognostic of tumor recurrence include HSPD1, MRPL15, MRPL4, AKAP1, PTRH2, COX4I1, GRPEL1, HSPA9, MRPS16, ENO1, TALDO1, TIGAR, and ENO2. Biomarker prognostic of distant metastasis include HSPD1, GRPEL1, MRPL15, MRPS16, COX4I1, ENO2, and ENO1. It should be appreciated that one or more of these biomarkers may be used under the present approach, and that some embodiments may use a combination of these biomarkers. One or more mitochondrial biogenesis inhibitors as described herein may be used to reduce and/or eliminate the Tamoxifen resistance. One or more mitochondrial biogenesis inhibitors may also be used to reduce and/or eliminate the risk of distant metastasis and/or tumor recurrence resulting from Tamoxifen resistance. A pharmaceutically effective amount of the mitochondrial biogenesis inhibitor(s) may be administered in response to an elevated level of one or more biomarkers having prognostic value of endocrine therapy failure, relative to a threshold or baseline level. It should be appreciated that the pharmaceutically effective amount may be determined using methods known in the art, without undue experimentation.

It should be appreciated that biomarker levels may be measured using assays known to those having ordinary skill in the art. Up-regulation of one or more of the biomarkers having prognostic value with respect to endocrine therapy resistance, tumor recurrence, and/or metastasis, may be used as an indicator that treatment with at least one mitochondrial biogenesis inhibitor may be effective, at treating the endocrine therapy resistance, improving the effectiveness of the endocrine therapy, and/or in conjunction with an endocrine therapy as part of a cancer treatment. Gene expression may be measured based on the protein gene product, and common techniques include expression proteomics, Western blotting, and enzyme-linked immunosorbent assay (sometimes referred to as the ELISA assay). Gene expression may also be measured based on mRNA levels, and common techniques for mRNA level measurement include Northern blotting and reverse transcription then quantitative polymerase chain reaction (also called RT-qPCR). The threshold or baseline level(s) may be obtained from available literature and/or databases known in the art. Also, the threshold or baseline level(s) may be obtained from using an assay on a biologic sample representing a normal, healthy cell line. As those having at least an ordinary level of skill in the art will appreciate, the threshold or baseline level(s) may also be determined from in vivo data of breast cancer patients having no symptoms of resistance to endocrine therapies, such as Tamoxifen.

The following paragraphs describe the methodologies and materials used in connection with the foregoing. The human breast cancer cell line (MCF7) was obtained commercially from the ATCC. The cell line was maintained in Dulbecco's Modified Eagle Medium (DMEM; GIBCO) supplemented with 10% HiFBS, 1% Glutamax and 1% Penicillin-Streptomycin, at 37° C. in 5% CO2.

Lentiviral gene transduction: Lentiviral vectors for the gene expression studies were all custom-built to specification by GeneCopoeia. The cDNA's encoding ESR1 (catalogue number: A0322; NM_001122742.1) or ErbB2 (catalogue number: Z2866; NM_004448.2) were inserted into the expression vector Lv-105-puro$^R$, containing a puromycin gene resistance cassette. Two vectors encoding ESR1 mutants (Y537S and Y537N) were also generated by site-directed mutagenesis and were confirmed by DNA-sequencing. Packaging cells (293Ta) and all reagents were purchased from GeneCopoeia Inc., respectively. After 48 hours of seeding and culture, 293Ta packaging cells were transfected with lentiviral vectors encoding ESR1, ESR1-Y537S, ESR1-Y537N, ErbB2, or empty vector EV (EX-NEG-Lv105), using Lenti-Pac™ HIV Expression Packaging Kit, according to the manufacturer's instructions. Two days post-transfection, lentivirus-containing culture medium was passed through a 0.45 µm filter and added to the target cells (MCF7 cells) in the presence of 5 µg/ml Polybrene. Infected cells were selected with a concentration of 1.5 µg/ml of puromycin (17). These cell lines were generated, while working at the University of Manchester, at the Paterson Institute (MF, FS and MPL).

Sulfo-rhodamine B (SRB) assay: SRB measures total biomass by staining cellular proteins. After 5 days treatment with of 4-OH-Tamoxifen (4-OHT, Sigma, cells were fixed in 10% trichloroacetic acid (T9159, Sigma) for 1 h at 4° C., stained with SRB (S9012, Sigma) for 15 minutes, and washed 3 times with 1% acetic acid (27225, Sigma). The incorporated dye was solubilized with 10 mM Tris-HCl, pH 8.8 (T1503, Sigma). Absorbance was spectrophotometrically measured at 540 nm in a FluoStar Omega plate reader (BMG Labtech). Background measurements were subtracted from all values.

MCF7 3D-mammosphere formation: A single cell suspension was prepared using enzymatic (1x Trypsin-EDTA, Sigma Aldrich, #T3924), and manual disaggregation (25 gauge needle). Cells were plated at a density of 500 cells/$cm^2$ in mammosphere medium (DMEM-F12+B27+20 ng/ml EGF+PenStrep) under non-adherent conditions, in culture dishes pre-coated with (2-hydroxyethylmethacrylate) (poly-HEMA, Sigma, #P3932), called "mammosphere plates." Then, the cells were pre-treated for 72 hours with 1 µM of 4-OH-Tamoxifen. Vehicle alone (DMSO) control cells were processed in parallel. Afterwards, they were trypsined and seeded in mammosphere plates. Cells were grown for 5 days and maintained in a humidified incubator at 37° C. After 5 days of culture, 3D-spheres>50 µm were counted using an eye piece ("graticule"), and the percentage of cells plated which formed spheres was calculated and is referred to as percent mammosphere formation, and was normalized to one (1=100% MSF).

Annexin-V analysis: Cell death was quantified by flow cytometry using propidium iodide (PI) and Annexin V-FITC (20). Briefly, $1.5 \times 10^5$ all the transfected cells were plated in 6 multi-well plate in complete media supplemented with 10% HiFBS. The next day, cells were treated with 1 µM of 4-OH-Tamoxifen (4-OHT) for 48 h and 72 h. Vehicle alone (DMSO) for control cells were processed in parallel. After 48 hours, cells were harvested and washed in cold phosphate-buffered saline (PBS). Cells were re-centrifuged and supernatants were discarded. Then, cells were re-suspended in 100 µl of annexin-binding buffer. Then, the annexing FITC conjugate (5 µl) and PI (1 µL) were added and incubated in the dark at room temperature for 15 min. After the incubation period, reaction was stopped by adding 400 µL of annexin-binding buffer. Cells were then analyzed by flow cytometry using a PE Texas Red signal detector for PI staining and a FITC signal detector to detect Annexin V binding. 30,000 events were recorded by FACS using Fortessa BD. Results are the average of three experiments that were performed in triplicate, three times independently.

Seahorse XFe96 metabolic flux analysis: Real-time oxygen consumption rates (OCR) and extracellular acidification rates (ECAR) rates in all transfected cells treated with 1 µM of 4-OHT for 48 h were determined using the Seahorse Extracellular Flux (XFe96) analyzer (Seahorse Bioscience, USA) (21). Briefly, $1.5 \times 10^4$ cells per well were seeded into XFe96 well cell culture plates, and incubated overnight to allow cell attachment. Then, cells were treated with 1 µM of 4-OHT for 48 h. Empty vector (EV) control cells were processed in parallel. After 48 hours of incubation, cells were washed in pre-warmed XF assay media (or for OCR measurement, XF assay media supplemented with 10 mM glucose, 1 mM Pyruvate, 2 mM L-glutamine and adjusted at 7.4 pH). Cells were then maintained in 175 µL/well of XF assay media at 37° C., in a non-$CO_2$ incubator for 1 hour. During the incubation time, we loaded 25 µM of 80 mM glucose, 9 µM oligomycin, and 1M 2-deoxyglucose (for ECAR measurement) or 10 µM oligomycin, 9 µM FCCP, 10 µM rotenone, 10 µM antimycin A (for OCR measurement), in XF assay media into the injection ports in the XFe96 sensor cartridge. Measurements were normalized by protein content (Bradford assay). Data sets were analyzed using XFe96 software and GraphPad Prism software, using one-way ANOVA and Student's t-test calculations. All experiments were performed in quintuplicate, three times independently.

Mitochondrial staining: Mitochondrial activity was assessed with MitoTracker Orange (#M7510, Invitrogen), whose accumulation in mitochondria is dependent upon membrane potential. Mitochondrial mass was determined using MitoTracker Deep-Red (#M22426, Invitrogen), localizing to mitochondria regardless of mitochondrial membrane potential. MCF7 transfected cells were seeded for 48 hours. MCF7-EV control cells were processed in parallel. After 48 hours, cells were incubated with pre-warmed MitoTracker staining solution (diluted in PBS/CM to a final concentration of 10 nM) for 30-60 minutes at 37° C. All subsequent steps were performed in the dark. Cells were washed in PBS, harvested, and re-suspended in 300 µL of PBS/CM. Cells were then analyzed by flow cytometry. Data analysis was performed using FlowJo software.

Label-free unbiased semi-quantitative proteomics analysis: Cell lysates were prepared for trypsin digestion by sequential reduction of disulphide bonds with TCEP and alkylation with MMTS. Then, the peptides were extracted and prepared for LC-MS/MS. All LC-MS/MS analyses were performed on an LTQ Orbitrap XL mass spectrometer (Thermo Scientific, San Jose, Calif.) coupled to an Ultimate 3000 RSLCnano system (Thermo Scientific, formerly Dionex, The Netherlands). Xcalibur raw data files acquired on the LTQ-Orbitrap XL were directly imported into Progenesis LCMS software (Waters Corp., Milford, Mass., formerly Non-linear dynamics, Newcastle upon Tyne, UK) for peak detection and alignment. Data were analyzed using the Mascot search. Five technical replicates were analyzed for each sample type.

Ingenuity pathway analysis (IPA): Unbiased interrogation and analysis of our proteomic data sets was carried out by employing a bioinformatics platform, known as Ingenuity Pathway Analysis (IPA) (Ingenuity systems, http://www.ingenuity.com). IPA assists with data interpretation, via the grouping of differentially expressed genes or proteins into known functions and pathways. Pathways with a z score of >+2 were considered as significantly activated, while pathways with a z score of <−2 were considered as significantly inhibited.

Quantification and Statistical Analysis: All analyses were performed with GraphPad Prism 6. Data were presented as mean±SD (±SEM for OCR and ECAR profiles, see FIGS. 5 and 6). All experiments were conducted at least three times, with ≥3 technical replicates per experiment, unless otherwise stated with representative data shown. Statistically significant differences were determined using the Student's t test or the analysis of variance (ANOVA) test. For the comparison among multiple groups, one-way ANOVA were used to determine statistical significance. P≤0.05 was considered significant and all statistical tests were two-sided.

Kaplan-Meier (K-M) analyses: To perform K-M analysis on metabolic gene transcripts, we used an open-access online survival analysis tool to interrogate publically available microarray data from up to 3,455 breast cancer patients. This allowed us to determine their prognostic value. For this purpose, we primarily analyzed data from ER(+) patients that were LN(+) at diagnosis and were of the luminal A sub-type, that were primarily treated with tamoxifen and not other chemotherapy (N=152 patients). In this group, 100% the patients received some form of endocrine therapy and ~95% of them received tamoxifen. Biased and outlier array data were excluded from the analysis. This allowed us to identify metabolic gene transcripts, with significant prognostic value. Hazard-ratios were calculated, at the best auto-selected cut-off, and p-values were calculated using the log-rank test and plotted in R. K-M curves were also generated online using the K-M-plotter (as high-resolution TIFF files), using univariate analysis: http://kmplot.com/analysis/index.php?p=service&cancer=breast. This allowed us to directly perform in silico validation of these metabolic biomarker candidates. The 2017 version of the database was utilized for all these analyses, while virtually identical results were also obtained with the 2014 and 2012 versions.

The invention may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

What is claimed is:

1. A method for identifying and treating endocrine therapy resistance due to the Y537S mutation of estrogen receptor ESR1 in a breast cancer, the method comprising:
    obtaining a biological epithelial sample of the cancer from a patient;
    determining, or having determined, the level of a plurality of biomarkers prognostic of endocrine therapy resistance in the biological epithelial sample selected from HSPD1, GRPEL1, MRPL15, MRPS16, COX4I1, ENO1, ENO2, MRPL4, AKAP1, PTRH2, HSPA9, and TALDO1;
    comparing the determined level to a threshold level from MCF7 cells transduced with ESR1 (wild type) for the plurality of biomarkers; and
    administering to the patient a pharmaceutically effective amount of a combination of an oxidative metabolism inhibitor and a glycolytic metabolism inhibitor if the determined level exceeds the threshold level.

2. The method of claim 1, wherein the plurality of biomarkers prognostic of endocrine therapy comprises a plurality of biomarkers prognostic of endocrine therapy resistance selected from HSPD1, GRPEL1, MRPL15, MRPS16, COX4I1, ENO1, and ENO2.

3. The method of claim 1, wherein the plurality of biomarkers prognostic of endocrine therapy resistance comprises at least one of (i) a biomarker prognostic of tumor recurrence and (ii) a biomarker prognostic of distant metastasis.

4. The method of claim 1, wherein the plurality of biomarkers prognostic of endocrine therapy resistance comprises at least one biomarker prognostic of tumor recurrence, and at least one biomarker prognostic of distant metastasis.

5. The method of claim 3, wherein the plurality of biomarkers prognostic of tumor recurrence comprises at least one of HSPD1, MRPL15, MRPL4, AKAP1, PTRH2, COX4I1, GRPEL1, HSPA9, MRPS16, ENO1, TALDO1, and ENO2.

6. The method of claim 3, wherein the plurality of biomarkers prognostic of distant metastasis comprises at least one of HSPD1, GRPEL1, MRPL15, MRPS16, COX4I1, ENO2, and ENO1.

7. The method of claim 1, wherein the the combination comprises:
    an oxidative metabolism inhibitor selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and
    a glycolytic metabolism inhibitor selected from the group comprising: a glycolysis inhibitor, an OXPHOS inhibitor, and an autophagy inhibitor.

8. The method of claim 7, wherein the glycolytic metabolism inhibitor is at least one of the following:
    a glycolysis inhibitor comprising one of 2-deoxy-glucose, ascorbic acid, and stiripentol;
    an OXPHOS inhibitor comprising one of atoravaquone, irinotecan, sorafenib, niclosamide, and berberine chloride; and
    an autophagy inhibitor comprising chloroquine.

9. The method of claim 7, wherein the combination comprises doxycycline, azithromycin, and ascorbic acid.

10. A method for identifying and treating endocrine therapy resistance due to the Y537S mutation of estrogen receptor ESR1 in a breast cancer, the method comprising:
    obtaining a biological epithelial sample of the cancer from a patient;
    determining, or having determined, the level of a plurality of biomarkers prognostic of endocrine therapy resistance in the biological epithelial sample selected from HSPD1, GRPEL1, MRPL15, MRPS16, COX4I1, ENO1, ENO2, MRPL4, AKAP1, PTRH2, HSPA9, TALDO1, and TIGAR;
    comparing the determined level to a threshold level from MCF7 cells transduced with ESR1 (wild type) for the plurality of biomarkers; and
    administering to the patient a pharmaceutically effective amount of a combination of an oxidative metabolism inhibitor and a glycolytic metabolism inhibitor if the determined level exceeds the threshold level,
    wherein the oxidative metabolism inhibitor is selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and the glycolytic metabolism inhibitor is selected from the group comprising: a glycolysis inhibitor, an OXPHOS inhibitor, and an autophagy inhibitor.

11. The method of claim 10, wherein the a plurality of biomarkers prognostic of endocrine therapy comprises a plurality of biomarkers prognostic of endocrine therapy resistance selected from HSPD1, MRPL15, COX4|1, GRPEL1, MRPS16, ENO1, and ENO2.

12. A method for increasing the effectiveness of an endocrine therapy on a breast cancer having the Y537 mutation of estrogen receptor ESR1, the method comprising:
    obtaining a biological epithelial sample of the cancer from a patient;
    determining, or having determined, the level of a plurality of biomarkers prognostic of endocrine therapy resistance in the biological epithelial sample selected from HSPD1, GRPEL1, MRPL15, MRPS16, COX4|1, ENO1, ENO2, MRPL4, AKAP1, PTRH2, HSPA9, TALDO1, and TIGAR;
    comparing the determined level to a threshold level from MCF7 cells transduced with ESR1 (wild type) for the plurality of biomarkers; and
    administering to the patient, in conjunction with an endocrine therapy, a pharmaceutically effective amount of a combination of an oxidative metabolism inhibitor and a glycolytic metabolism inhibitor if the determined level exceeds the threshold level.

13. The method of claim 12, wherein the endocrine therapy comprises Tamoxifen.

14. The method of claim 12, wherein the biomarker prognostic of endocrine therapy resistance comprises a plurality of biomarkers prognostic of endocrine therapy resistance selected from HSPD1, MRPL15, COX4|1, GRPEL1, MRPS16, ENO1, and ENO2.

15. The method of claim 12, wherein:
    the oxidative metabolism inhibitor is selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and
    the glycolytic metabolism inhibitor is selected from the group comprising: a glycolysis inhibitor, an OXPHOS inhibitor, and an autophagy inhibitor.

16. A method for treating breast cancer having the Y537S mutation of estrogen receptor ESR1, the method comprising:
    obtaining a biological epithelial sample of the cancer from a patient;
    determining, or having determined, the level of a plurality of biomarkers prognostic of endocrine therapy resistance in the biological epithelial sample selected from HSPD1, GRPEL1, MRPL15, MRPS16, COX4|1, ENO1, ENO2, MRPL4, AKAP1, PTRH2, HSPA9, TALDO1, and TIGAR;
    comparing the determined level to a threshold level from MCF7 cells transduced with ESR1 (wild type) for the plurality of biomarkers; and
    administering to the patient, in conjunction with an endocrine therapy, a pharmaceutically effective amount of a combination of an oxidative metabolism inhibitor and a glycolytic metabolism inhibitor if the determined level exceeds the threshold level.

17. The method of claim 16, wherein the endocrine therapy comprises Tamoxifen.

18. The method of claim 16, wherein the cancer comprises breast cancer.

19. The method of claim 16, wherein the biomarker prognostic of endocrine therapy resistance comprises a plurality of biomarkers prognostic of endocrine therapy resistance selected from HSPD1, MRPL15, COX4|1, GRPEL1, MRPS16, ENO1, and ENO2.

20. A method for treating breast cancer endocrine therapy resistance due to the Y537S mutation of estrogen receptor ESR1, the method comprising:
    determining, or having determined, the level in a biological epithelial sample from a patient, of a plurality of biomarkers prognostic of endocrine therapy resistance in a biological epithelial sample selected from HSPD1, GRPEL1, MRPL15, MRPS16, COX4|1, ENO1, ENO2, MRPL4, AKAP1, PTRH2, HSPA9, TALDO1, and TIGAR;
    comparing the determined level to a threshold level from MCF7 cells transduced with ESR1 (wild type) for the plurality of biomarkers; and
    administering to the patient a pharmaceutically effective amount of a combination of an oxidative metabolism inhibitor and a glycolytic metabolism inhibitor if the determined level exceeds the threshold level.

21. The method of claim 20, wherein at least one biomarker prognostic of endocrine therapy resistance is up-regulated.

22. The method of claim 20, wherein the endocrine therapy comprises Tamoxifen.

23. The method of claim 21, wherein the biomarker prognostic of endocrine therapy resistance comprises a plurality of biomarkers prognostic of endocrine therapy resistance selected from HSPD1, MRPL15, COX4|1, GRPEL1, MRPS16, ENO1, and ENO2.

24. The method of claim 20, wherein:
    the oxidative metabolism inhibitor is selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and
    the glycolytic metabolism inhibitor is selected from the group comprising: a glycolysis inhibitor, an OXPHOS inhibitor, and an autophagy inhibitor.

25. A method of treating breast cancer in a patient having an upregulated expression of a plurality of biomarkers prognostic of endocrine therapy resistance selected from epithelial HSPD1, GRPEL1, MRPL15, MRPS16, COX4|1, ENO1, ENO2, MRPL4, AKAP1, PTRH2, HSPA9, and TALDO1, the method comprising administering a pharmaceutically effective amount of a combination of an oxidative metabolism inhibitor and a glycolytic metabolism inhibitor.

26. The method of claim 25, wherein the biomarkers prognostic of endocrine therapy resistance comprises a plurality of biomarkers prognostic of endocrine therapy resistance selected from HSPD1, MRPL15, COX4|1, GRPEL1, MRPS16, ENO1, and ENO2.

27. The method of claim 25, wherein:
    the oxidative metabolism inhibitor is selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and the glycolytic metabolism inhibitor is selected from the group comprising: a glycolysis inhibitor, an OXPHOS inhibitor, and an autophagy inhibitor.

28. A method of treating a patient's breast cancer in cancer cells having a resistance to endocrine therapy due to the Y537S mutation of estrogen receptor ESR1, the method comprising administering to the patient a pharmaceutically effective amount of a combination of an oxidative metabolism inhibitor and a glycolytic metabolism inhibitor;
wherein an epithelial biological sample of the cancer cells have an up-regulated expression of a plurality of biomarkers prognostic of endocrine therapy resistance selected from HSPD1, MRPL15, MRPL4, AKAP1, PTRH2, COX4I1, GRPEL1, HSPA9, MRPS16, ENO1, TALDO1, and ENO2.

29. The method of claim 28, wherein:
the oxidative metabolism inhibitor is selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and
the glycolytic metabolism inhibitor is selected from the group comprising: a glycolysis inhibitor, an OXPHOS inhibitor, and an autophagy inhibitor.

30. The method of claim 28, wherein the epithelial biological sample of the cancer cells has an up-regulated expression of a plurality of biomarkers prognostic of endocrine therapy resistance selected from of HSPD1, MRPL15, COX4I1, GRPEL1, MRPS16, ENO1, and ENO2.

31. A method of increasing the effectiveness of an endocrine therapy on breast cancer cells having the Y537S mutation of estrogen receptor ESR1, the method comprising administering a pharmaceutically effective amount of a combination of an oxidative metabolism inhibitor and a glycolytic metabolism inhibitor;
wherein an epithelial biological sample of the cancer cells has an up-regulated expression of a plurality of biomarkers prognostic of endocrine therapy resistance selected from HSPD1, MRPL15, MRPL4, AKAP1, PTRH2, COX4I1, GRPEL1, HSPA9, MRPS16, ENO1, TALDO1, and ENO2.

32. The method of claim 31, wherein:
the oxidative metabolism inhibitor is selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and
the glycolytic metabolism inhibitor is selected from the group comprising: a glycolysis inhibitor, an OXPHOS inhibitor, and an autophagy inhibitor.

33. A method of treating breast cancer having the Y537S mutation of estrogen receptor ESR1, the method comprising administering at least one endocrine therapy and a combination of an oxidative metabolism inhibitor and a glycolytic metabolism inhibitor, wherein an epithelial biological sample of the cancer has an up-regulated expression of a plurality of biomarkers prognostic of endocrine therapy resistance selected from HSPD1, MRPL15, MRPL4, AKAP1, PTRH2, COX4I1, GRPEL1, HSPA9, MRPS16, ENO1, TALDO1, and ENO2.

34. The method of claim 33, wherein:
the oxidative metabolism inhibitor is selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and
the glycolytic metabolism inhibitor is selected from the group comprising: a glycolysis inhibitor, an OXPHOS inhibitor, and an autophagy inhibitor.

35. The method of claim 33, wherein the endocrine therapy comprises Tamoxifen.

* * * * *